United States Patent
Miyakoshi et al.

(10) Patent No.: US 10,556,967 B2
(45) Date of Patent: Feb. 11, 2020

(54) ANTI-ADAM28 ANTIBODY FOR TREATING CANCER

(71) Applicants: GENEFRONTIER CORPORATION, Kashiwa-shi, Chiba (JP); KEIO UNIVERSITY, Tokyo (JP)

(72) Inventors: Akira Miyakoshi, Kashiwa (JP); Rena Matsumoto, Kashiwa (JP); Shizue Katoh, Kashiwa (JP); Yuki Hayami, Kashiwa (JP); Satsuki Mochizuki, Tokyo (JP); Masayuki Shimoda, Tokyo (JP); Yasunori Okada, Tokyo (JP)

(73) Assignees: GENEFRONTIER CORPORATION, Kashiwa (JP); KEIO UNIVERSITY, Tokyo (JP)

( * ) Notice: Subject to any disclaimer, the term of this patent is extended or adjusted under 35 U.S.C. 154(b) by 23 days.

(21) Appl. No.: 15/815,148

(22) Filed: Nov. 16, 2017

(65) Prior Publication Data

US 2018/0155448 A1    Jun. 7, 2018

Related U.S. Application Data

(63) Continuation of application No. 14/440,391, filed as application No. PCT/JP2013/076745 on Oct. 1, 2013, now Pat. No. 9,845,364.

(60) Provisional application No. 61/724,484, filed on Nov. 9, 2012.

(51) Int. Cl.
| | |
|---|---|
| A61K 39/395 | (2006.01) |
| C07K 16/00 | (2006.01) |
| C07K 16/40 | (2006.01) |
| C07K 16/28 | (2006.01) |
| A61K 39/00 | (2006.01) |

(52) U.S. Cl.
CPC .......... *C07K 16/40* (2013.01); *C07K 16/2896* (2013.01); *A61K 2039/505* (2013.01); *C07K 2317/21* (2013.01); *C07K 2317/24* (2013.01); *C07K 2317/34* (2013.01); *C07K 2317/55* (2013.01); *C07K 2317/56* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,530,101 A | 6/1996 | Queen et al. |
| 2009/0053213 A1 | 2/2009 | Steidl et al. |
| 2009/0252733 A1 | 10/2009 | Tesar |

FOREIGN PATENT DOCUMENTS

| | | | |
|---|---|---|---|
| CN | 101218255 A | 7/2008 | |
| CN | 101287764 A | 10/2008 | |
| WO | WO-2008077993 A1 * | 7/2008 | ............... B82Y 5/00 |

OTHER PUBLICATIONS

Mochizuki et al. Selective Inhibition of ADAM28 Suppresses Lung Carcinoma Cell Growth and Metastasis. Mol Cancer Ther; 17(11); 1-12. (Year: 2018).*
Campbell A, General properties and applications of monoclonal antibodies, Elsevier Science Publishers, section 1.1, pp. 1-32, 1984. (Year: 1984).*
Herat et al., "The Metalloproteinase ADAM28 Promotes Metabolic Dysfunction in Mice," *Int. J. Mol. Sci.*, 18(4): E884 (2017).
Jowett et al., "ADAM28 is elevated in humans with the metabolic syndrome and is a novel sheddase of human tumour necrosis factor-α," *Immunol. Cell Biol.*, 90(10): doi: 10.1038/icb.2012.44 (2012).
Miyamae et al., "ADAM28 is expressed by epithelial cells in human normal tissues and protects from C1q-induced cell death," *FEBS J.*, 283(9): 1574-1594 (2016).
Mochizuki et al., "Connective tissue growth factor is a substrate of ADAM28," *Biochem. Biophys. Res. Commun.*, 402(4): 651-657 (2010).
Rudnicka et al., "Overexpression and knock-down studies highlight that a disintegrin and metalloproteinase 28 controls proliferation and migration in human prostate cancer," *Medicine (Baltimore)*, 95(40): e5085 (2016).
U.S. Appl. No. 14/440,391, filed May 4, 2015.
Abe et al., *The American Journal of Pathology*, 183(5): 1667-1678 (2013).
Abe et al., "ADAM28 expression in oncogene-transformed cells and human carcinoma cells," *XXIIIrd FECTS and ISMB Joint Meeting*, Abstract P5.1 (Katowice, Poland, Aug. 25-29, 2012).
Bridges et al., *Biochem. J.*, 387: 101-108 (2005).
Bridges et al., *The Journal of Biological Chemistry*, 277(5): 3784-3792 (2002).
Brown et al., *J. Immunol.*, 156: 3285-3291 (May 1996).
Fourie et al., *The Journal of Biological Chemistry*, 278(33): 30469-30477 (2003).
Hikichi et al., *Biochemical and Biophysical Research Communications*, 386: 294-299 (2009).
Howard et al., *Biochem. J.*, 348: 21-27 (2000).
Kuroda et al., *International Journal of Cancer*, 127: 1844-1856 (2010).

(Continued)

*Primary Examiner* — Maher M Haddad
(74) *Attorney, Agent, or Firm* — Leydig, Voit & Mayer, Ltd.

(57) ABSTRACT

The present invention provides an antibody that specifically binds to human ADAM28, inhibits enzyme activity of human ADAM28, and has an activity to suppress metastasis of a cancer cell that expresses human ADAM28. The antibody of the present invention can be a human antibody.

14 Claims, 3 Drawing Sheets
Specification includes a Sequence Listing.

(56) References Cited

OTHER PUBLICATIONS

Mitsui et al., *Cancer Research*, 66: 9913-9920 (2006).
Mochizuki et al., *Biochemical and Biophysical Research Communications*, 315: 79-84 (2004).
Mochizuki et al., *Biochemical and Biophysical Research Communications*, 402: 651-657 (2010).
Mochizuki et al., *Cancer Science*, 98(5): 621-628 (2007).
Mochizuki et al., *J. Natl. Cancer Inst.*, 104(12): 906-922 (2012).
Mochizuchi et al., *J. Natl. Cancer Inst.*, 104(12): 906-922 (Jun. 20, 2012).
Mochizuchi et al., "Effects of human antibodies against ADAM28 on cancer cell growth and metastasis," *The 1st MBE (Matrix Biology Europe) Conference organized by The Dutch Society for Matrix Biology (NVMB), The Netherlands Institute for Regenerative Medicine (NIRM) and the International Society for Matrix Biology (ISMB)*, p. 152, Abstract 116 (Jun. 21-14, 2014).
Ohtsuka et al., *Int. J. Cancer*, 118: 263-273 (2006).
Roemer et al., *Oncology Reports*, 11: 529-536 (2004).
Roemer et al., *The Journal of Urology*, 172: 2162-2166 (2004).
Rothe et al., *J. Mol. Biol.*, 376: 1182-1200 (2008).
Shimoda et al., *The Journal of Biological Chemistry*, 282(35): 25864-25874 (2007).
Takeda et al., *EMBO J.*, 25(11): 2388-2396 (2006).
Uniprot, "Disintegrin and metalloproteinase domain-containing protein 28 (ADAM28)," UniProtKB Accession No. Q9UKQ2 (ADA28_HUMAN) (published Jun. 20, 2001).
Vajdos et al., *J. Mol. Biol.*, 320(2):415-428 (Jul. 5, 2002).
Zucker et al., *J. Natl. Cancer Inst.*, 104(12): 887-888 (2012).
Japanese Patent Office, International Search Report in International Patent Application No. PCT/JP2013/076745 (dated Dec. 3, 2013).
Mochizuki et al., "ADAM28 as a Target for Human Cancers," *Curr. Pharm. Des.*, 15(20): 2349-2358 (2009).
European Patent Office, Extended European Search Report in European Patent Application No. 18211128.6 (dated Feb. 22, 2019).

\* cited by examiner

A. In vitro inhibition assay along with change of the ratio of ADAM28 : 211-12

B. In vitro inhibition assay along with change of the ratio of ADAM28 : 211-14

ANTI-ADAM28 ANTIBODY FOR TREATING CANCER

CROSS-REFERENCE TO RELATED APPLICATIONS

This patent application is a continuation of U.S. patent application Ser. No. 14/440,391, filed on May 4, 2015, which is the U.S. national phase of International Patent Application No. PCT/JP2013/076745, filed Oct. 1, 2013, which claims the benefit of U.S. Provisional Patent Application No. 61/724,484, filed on Nov. 9, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 73,215 bytes ASCII (Text) file named "736187SequenceListing.txt," created Nov. 6, 2017.

TECHNICAL FIELD

The present invention relates to an anti-human ADAM28 antibody, and pharmaceutical use thereof.

BACKGROUND ART

ADAM proteins (a disintegrin and metalloproteinases) are multifunctional proteins involved in the ectodomain shedding of transmembrane proteins, cell adhesion and infiltration (non-patent documents 1, 2). The human genome contains 25 ADAMs including four pseudogenes and 21 kinds of ADAMs are composed of 13 kinds of proteolytic ADAMs that exhibit proteolytic activity and eight kinds of non-proteolytic ADAMs (non-patent documents 1, 3). Proteolytic ADAMs share the metalloproteinase domain of matrix metalloproteinases (MMPs), and a typical proteolytic ADAM protein comprises propeptide, metalloproteinase, disintegrin-like, cysteine-rich, epidermal growth factor-like, transmembranes and cytoplasmic domains (non-patent documents 3-9). Many proteolytic ADAMs, including ADAM8, ADAM9, ADAM12, ADAM15, ADAM17, ADAM19 and ADAM28 are overexpressed in human cancers and are associated with tumor growth and progression (non-patent documents 5, 9). The present inventors' previous studies have indicated that ADAM28 (also known as ADAM metallopeptidase domain 28), which has two alternative isoforms, including a prototype membrane-anchored form (ADAM28m) and a short secreted form (ADAM28s) (non-patent documents 5, 10, 11), is abundantly expressed in human non-small cell lung and breast carcinomas (non-patent documents 12, 13). By in situ hybridization and immunohistochemistry, the present inventors have demonstrated that ADAM28 is expressed predominantly in carcinoma cells contained in carcinoma tissues and that the mRNA expression levels of ADAM28 are associated with the cellular proliferation of breast cancer (non-patent document 13) and with both cancer cell proliferation and infiltration in non-small cell lung cancer (non-patent document 12). In a parallel study, the present inventors showed that serum ADAM27 levels in non-small cell lung cancer patients substantially increase with the progression of tumor, lymph node metastasis, and cancer recurrence (non-patent document 14). These data imply that ADAM28 is involved in cell proliferation and metastasis particularly in human cancer. The present inventors have demonstrated that ADAM28 contributes to cancer cell proliferation through enhanced bioavailability of insulin-like growth factor-I (IGF-I) by selective digestion of IGF-binding protein-3 (IGFBP-3) of IGF-I/IGFBP-3 complex (non-patent document 13), and to angiogenesis by digestion of connective tissue growth factor in breast cancer (non-patent document 15).

The phage display method is one of the display techniques that have realized a in vitro high-speed selection by forming a one-to-one correspondence in the form of phage particles between a functional peptide or protein and a DNA encoding same. This phage display method has been applied to antibody selection, and many antibodies obtained by this method have been developed as medicaments (non-patent document 16). Furthermore, a method of obtaining a specific antibody by combining a human artificial antibody library and a phage display method has also been established, and such methods have been practicalized by plural companies, as evidenced by HuCAL (Human Combinatorial Antibody Library) of MorphoSys.

DOCUMENT LIST

Non-Patent Documents non-patent document 1: Mol Aspects Med. 2008; 29 (5): 258-289
non-patent document 2: Semin Cell Dev Biol. 2009; 20 (2): 138-145
non-patent document 3: Pathol Int. 2010; 60 (7): 477-496
non-patent document 4: Genes Dev. 2003; 17 (1): 7-30
non-patent document 5: Cancer Sci. 2007; 98 (5): 621-628
non-patent document 6: Nat Rev Mol Cell Biol. 2005; 6 (1): 32-43
non-patent document 7: Kelley's Textbook of Rheumatology. 8th ed. Philadelphia, Pa.: Elsevier Saunders; 2009: 115-134
non-patent document 8: Curr Opin Cell Biol. 2003; 15 (5): 598-606
non-patent document 9: Nat Rev Cancer. 2008; 8 (12): 929-941
non-patent document 10: J Biol Chem. 1999; 274 (41): 29251-29259
non-patent document 11: Curr Pharm Des. 2009; 15 (20): 2349-2358
non-patent document 12: Int J Cancer. 2006; 118 (2): 263-273
non-patent document 13: Cancer Res. 2006; 66 (20): 9913-9920
non-patent document 14: Int J Cancer. 2010; 127 (8): 1844-1856
non-patent document 15: Biochem Biophys Res Commun. 2010; 402 (4): 651-657
non-patent document 16: Rothe, C. et al. J. Mol. Biol. 2008; 376:1182-1200

SUMMARY OF THE INVENTION

Problems to be Solved by the Invention

An object of the present invention is to provide an anti-human ADAM28 antibody useful for the prophylaxis or treatment of cancer, or inhibition of cancer metastasis.

Means of Solving the Problems

To solve the above-mentioned problem, the present inventors have prepared plural anti-ADAM28 antibodies that bond to human ADAM28. As a result, they have found that some prepared anti-human ADAM28 antibodies inhibit enzyme activity of ADAM28 and show a superior suppressive effect on cancer cell proliferation and an inhibitory effect on cancer metastasis in in vivo model. Based on the above findings, they have conducted further studies and completed the present invention.

Accordingly, the present invention relates to the following.

[1] An antibody specifically binding to human ADAM28, and having an activity to inhibit enzyme activity of human ADAM28.

[2] The antibody of [1] that binds to human ADAM28 at an epitope comprising the amino acid sequence shown in SEQ ID NO: 21, 22 or 23.

[3] The antibody of [1], comprising a light chain variable region and a heavy chain variable region, wherein (1) the light chain variable region comprises CDR1 comprising the amino acid sequence shown in SEQ ID NO: 5, CDR2 comprising the amino acid sequence shown in SEQ ID NO: 6 and CDR3 comprising the amino acid sequence shown in SEQ ID NO: 7, and the heavy chain variable region comprises CDR1 comprising the amino acid sequence shown in SEQ ID NO: 8, CDR2 comprising the amino acid sequence shown in SEQ ID NO: 9 and CDR3 comprising the amino acid sequence shown in SEQ ID NO: 10;

(2) the light chain variable region comprises CDR1 comprising the amino acid sequence shown in SEQ ID NO: 5, CDR2 comprising the amino acid sequence shown in SEQ ID NO: 6 and CDR3 comprising the amino acid sequence shown in SEQ ID NO: 7, and the heavy chain variable region comprises CDR1 comprising the amino acid sequence shown in SEQ ID NO: 8, CDR2 comprising the amino acid sequence shown in SEQ ID NO: 9 and CDR3 comprising the amino acid sequence shown in SEQ ID NO: 10, except that 1 to 3 amino acids are substituted, deleted, inserted, and/or added in at least one amino acid sequence selected from the group consisting of the amino acid sequences shown in SEQ ID NOs: 5, 6 and 7, and/or 1 to 3 amino acids are substituted, deleted, inserted, and/or added in at least one amino acid sequence selected from the group consisting of the amino acid sequences shown in SEQ ID NOs: 8, 9 and 10;

(3) the light chain variable region comprises CDR1 comprising the amino acid sequence shown in SEQ ID NO: 11, CDR2 comprising the amino acid sequence shown in SEQ ID NO: 12 and CDR3 comprising the amino acid sequence shown in SEQ ID NO: 13, and the heavy chain variable region comprises CDR1 comprising the amino acid sequence shown in SEQ ID NO: 14, CDR2 comprising the amino acid sequence shown in SEQ ID NO: 15 and CDR3 comprising the amino acid sequence shown in SEQ ID NO: 16; or (4) the light chain variable region comprises CDR1 comprising the amino acid sequence shown in SEQ ID NO: 11, CDR2 comprising the amino acid sequence shown in SEQ ID NO: 12 and CDR3 comprising the amino acid sequence shown in SEQ ID NO: 13, and the heavy chain variable region comprises CDR1 comprising the amino acid sequence shown in SEQ ID NO: 14, CDR2 comprising the amino acid sequence shown in SEQ ID NO: 15 and CDR3 comprising the amino acid sequence shown in SEQ ID NO: 16, except that 1 to 3 amino acids are substituted, deleted, inserted, and/or added in at least one amino acid sequence selected from the group consisting of the amino acid sequences shown in SEQ ID NOs: 11, 12 and 13, and/or 1 to 3 amino acids are substituted, deleted, inserted, and/or added in at least one amino acid sequence selected from the group consisting of the amino acid sequences shown in SEQ ID NOs: 14, 15 and 16;

(5) the light chain variable region comprises CDR1 comprising the amino acid sequence shown in SEQ ID NO: 24, CDR2 comprising the amino acid sequence shown in SEQ ID NO: 25 and CDR3 comprising the amino acid sequence shown in SEQ ID NO: 26, and the heavy chain variable region comprises CDR1 comprising the amino acid sequence shown in SEQ ID NO: 27, CDR2 comprising the amino acid sequence shown in SEQ ID NO: 28 and CDR3 comprising the amino acid sequence shown in SEQ ID NO: 29; or (6) the light chain variable region comprises CDR1 comprising the amino acid sequence shown in SEQ ID NO: 24, CDR2 comprising the amino acid sequence shown in SEQ ID NO: 25 and CDR3 comprising the amino acid sequence shown in SEQ ID NO: 26, and the heavy chain variable region comprises CDR1 comprising the amino acid sequence shown in SEQ ID NO: 27, CDR2 comprising the amino acid sequence shown in SEQ ID NO: 28 and CDR3 comprising the amino acid sequence shown in SEQ ID NO: 29, except that 1 to 3 amino acids are substituted, deleted, inserted, and/or added in at least one amino acid sequence selected from the group consisting of the amino acid sequences shown in SEQ ID NOs: 24, 25 and 26, and/or 1 to 3 amino acids are substituted, deleted, inserted, and/or added in at least one amino acid sequence selected from the group consisting of the amino acid sequences shown in SEQ ID NOs: 27, 28 and 29.

[4] The antibody of [3], wherein (1') the light chain variable region comprises the amino acid sequence shown in SEQ ID NO: 17, and the heavy chain variable region comprises the amino acid sequence shown in SEQ ID NO: 18;

(3') the light chain variable region comprises the amino acid sequence shown in SEQ ID NO: 19, and the heavy chain variable region comprises the amino acid sequence shown in SEQ ID NO: 20; or (5') the light chain variable region comprises the amino acid sequence shown in SEQ ID NO: 30, and the heavy chain variable region comprises the amino acid sequence shown in SEQ ID NO: 31.

[5] A pharmaceutical composition comprising the antibody of any of [1]-[4].

[6] An agent for the prophylaxis or treatment of cancer, comprising the antibody of any of [1]-[4].

[7] A cancer metastasis inhibitor comprising the antibody of any of [1]-[4].

[8] A method of preventing or treating cancer in a mammal, comprising administering an effective amount of the antibody of any of [1]-[4] to the mammal.

[9] The method of [8], wherein the mammal is human.

[10] A method of inhibiting cancer metastasis in a mammal, comprising administering an effective amount of the antibody of any of [1]-[4] to the mammal.

[11] The method of [10], wherein the mammal is human.

[12] The antibody of any of [1]-[4] for use in the prophylaxis or treatment of cancer.

[13] The antibody of any of [1]-[4] for use in the inhibition of cancer metastasis.

[14] Use of the antibody of any of [1]-[4] for the production of an agent for the prophylaxis or treatment of cancer.

[15] Use of the antibody of any of [1]-[4] for the production of a cancer metastasis inhibitor.

[16] A polynucleotide encoding the antibody of any of [1]-[4].
[17] A vector comprising the polynucleotide of [16].
[18] A transformant comprising the vector of [17].

Effect of the Invention

According to the present invention, an anti-human ADAM28 antibody useful for the prophylaxis or treatment of cancer, or inhibition of cancer metastasis is provided.

DESCRIPTION OF EMBODIMENTS

Figure 1:
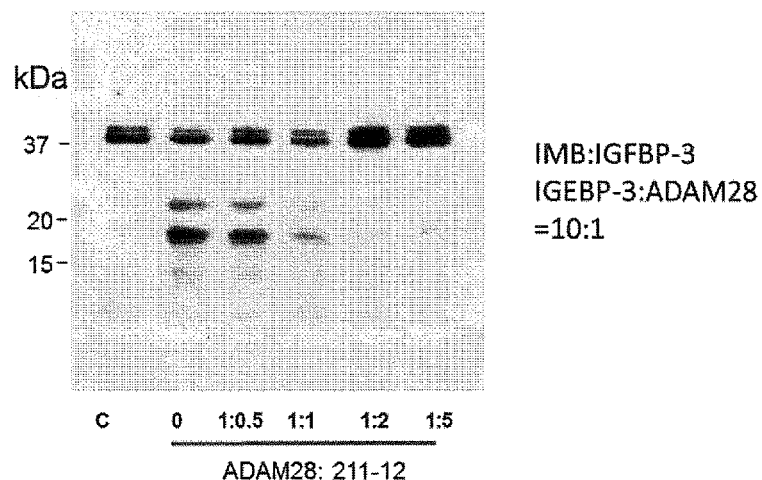
FIG. 1 shows of an enzyme activity inhibitory effect of anti-human ADAM28 antibody.
Figure 1:
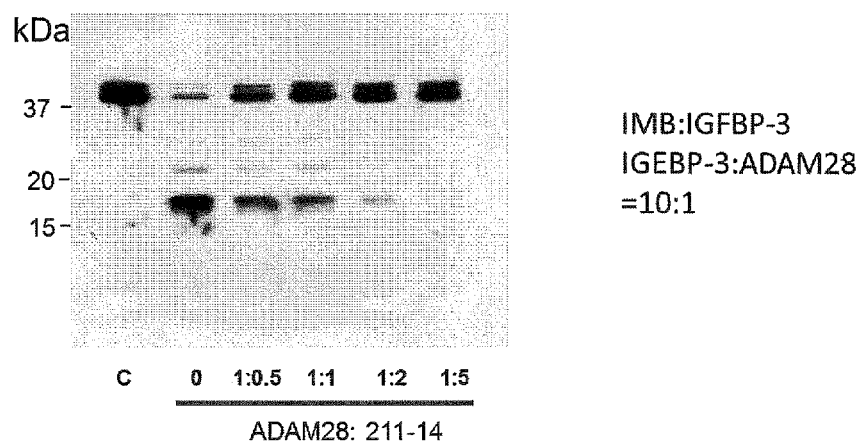

The present invention provides an antibody having a specific binding activity to human ADAM28, and an activity to inhibit enzyme activity of human ADAM28.

ADAM28 is a known protein, and the amino acid sequence thereof and the cDNA sequence thereof are also known. ADAM28 includes two kinds of a prototype membrane-anchored form (ADAM28m) and a short secretion form (ADAM28s), both of which are encompassed in ADAM28 in the present invention. A representative amino acid sequence of human ADAM28m is shown in SEQ ID NO: 2, a representative cDNA sequence of human ADAM28m is shown in SEQ ID NO: 1, a representative amino acid sequence of human ADAM28s is shown in SEQ ID NO: 4, and a representative cDNA sequence of human ADAM28s is shown in SEQ ID NO: 3.

The antibody of the present invention has a specific binding activity to human ADAM28.

The "human ADAM28" means that the amino acid sequence or nucleotide sequence of ADAM28 has the same or substantially the same amino acid sequence or nucleotide sequence as the amino acid sequence or nucleotide sequence of ADAM28 naturally expressed in human. Being "substantially the same" means that the amino acid sequence or nucleotide sequence of interest has not less than 70% (preferably not less than 80%, more preferably not less than 90%, more preferably not less than 95%, most preferably not less than 99%), identity with the amino acid sequence or nucleotide sequence of ADAM28 naturally expressed in human, and has the function of human ADAM28. Terms for biological species other than human, proteins other than ADAM28, gene and fragments thereof are also interpreted in the same manner.

The "specific binding" of an antibody to antigen X means that the binding affinity of an antibody to antigen X in an antigen-antibody reaction is higher than the binding affinity to a non-specific antigen (e.g., bovine serum albumin (BSA)).

The antibody of the present invention has an activity to inhibit the enzymatic activity of human ADAM28. The enzyme activity of human ADAM28 specifically means an activity of human ADAM28 to cleave human IGFBP-3 (Insulin-like Growth Factor Binding Protein-3). The activity of human ADAM28 to cleave human IGFBP-3 can be evaluated by, for example, the zymography analysis described in Cancer Res 2006; 66(20):9913-9920.

In the present specification, the "antibody" is used as one encompassing a full-length antibody and any antigen-binding fragment (i.e., "antigen-binding portion") thereof or a single chain thereof. The "antibody" refers to a glycoprotein containing at least two heavy chains (H) and two light chains (L), which are linked by a disulfide bond, or an antigen-binding portion thereof. Each heavy chain is constituted by a heavy chain variable region (to be abbreviated as $V_H$ herein) and a heavy chain constant region. The heavy chain constant region is constituted by 3 domains of $C_H1$, $C_H2$ and $C_H3$. Each light chain is constituted by a light chain variable region (to be abbreviated as $V_L$ herein) and a light chain constant region. The light chain constant region is constituted by a single domain $C_L$. $V_H$ and $V_L$ regions are further subdivided into regions with higher variability called complementarity determining regions (CDRs), which contain more highly conservative regions called framework regions (FRs) scattered therein. Each $V_H$ and $V_L$ is constituted by 3 CDRs and 4 FRs, which are aligned in the following order, i.e., FR1, CDR1, FR2, CDR2, FR3, CDR3, FR4 from the amino terminus to the carboxy terminus. The variable regions of said heavy chain and light chain contain binding domains that interact with an antigen. The constant region of an antibody can mediate the binding of immunoglobulin to host tissues or factors, including various cells (e.g., effector cells) of the immune system and the first component (C1q) of the conventional complement system.

In the present specification, the "antigen-binding portion" of an antibody is used to refer to one or more fragments of an antibody retaining an ability to specifically bind to an antigen (e.g., human ADAM28). It has been clarified that the antigen binding function of an antibody is performed by a fragment of a full-length antibody. Examples of the binding fragment included in the term "antigen binding portion" of an antibody include (i) Fab fragment, a monovalent fragment constituted by $V_L$, $V_H$, $C_L$ and $C_{H1}$ domains, (ii) F(ab')$_2$ fragment, a divalent fragment containing two Fab fragments linked by disulfide bond in the hinge region, (iii) Fab' fragment, an inherent Fab having a hinge region portion (see FUNDAMENTAL IMMUNOLOGY, Paul ed., 3. sup. rd ed. 1993), (iv) Fd fragment constituted by $V_H$ and $C_{H1}$ domains, (v) Fv fragment constituted by $V_L$ and $V_H$ domains in a single arm of an antibody, (vi) dAb fragment constituted by $V_H$ domain (Ward et al., (1989) Nature 341:544-546), (vii) isolated complementarity determining region (CDR) and (viii) nanobody which is a heavy chain variable region containing single variable domain and two constant regions. While $V_L$ and $V_H$, which are the two domains of Fv fragment, are encoded by different genes, they can be linked by a synthetic linker to produce a single protein chain from them by recombinant techniques, wherein, in this chain, $V_L$ and $V_H$ regions pair with each other to form a monovalent molecule (known as a single chain Fv (scFv); see, for example, Bird et al. (1988) Science 242: 423-426; and Huston et al., (1988) Proc. Natl. Acad. Sci. USA 85: 5879-5883). Such single chain antibody is also encompassed in the "antigen-binding portion" of an antibody. Such antibody fragments are obtained by those of ordinary skill in the art by known conventional techniques, and screened for usefulness in the same manner as with unmodified antibody.

The antibody of the present invention is preferably a monoclonal antibody. The "monoclonal antibody" refers to a preparation of an antibody molecule of a single molecule composition. The monoclonal antibody composition shows single binding-specificity and affinity for a particular epitope.

The antibody of the present invention is preferably a human antibody or humanized antibody. The "human antibody" refers to an antibody having variable regions derived from a human germline immunoglobulin sequence in both the framework and CDR regions. Furthermore, when an antibody contains a constant region, the constant region also derives from a human germline immunoglobulin sequence. In the present specification, the "human antibody" also encompasses even an embodiment including an amino acid residue not encoded by a human germline immunoglobulin sequence (e.g., mutation introduced by random or site-directed mutagenesis in vitro or somatic mutation in vivo).

In the present specification, in addition, the term of the "humanized antibody" means an antibody wherein a CDR sequence derived from the germline of an animal species other than human, such as mouse, is fused on the human framework sequence.

In the present specification, the human antibody encompasses a "reconstituted human antibody". The reconstituted human antibody refers to a modified antibody wherein at least one CDR contained in the first human donor antibody is used in the second human acceptor antibody, instead of CDR of the second human acceptor antibody. Preferably, all 6 CDRs are substituted. More preferably, the whole antigen binding region (e.g., Fv, Fab or F(ab')2) of the first human donor antibody is used instead of the corresponding region in the second human acceptor antibody. More preferably, the Fab region of the first human donor antibody is operably linked to an appropriate constant region of the second human acceptor antibody to form a full-length antibody.

The reconstituted human antibody can be produced by conventional gene recombinant techniques disclosed in, for example, EP125023, WO96/02576, the above-mentioned document 16 and the like. To be specific, for example, a DNA sequence designed to link a desired CDR in a donor human antibody and a desired framework region (FR) in an acceptor human antibody is synthesized by PCR method using, as primers, several oligonucleotides produced to have a region overlapping with the terminus regions of both CDR and FR (see the method described in WO98/13388). The obtained DNA is linked to a DNA encoding a human antibody constant region or a human antibody constant region mutant, which is incorporated into a expression vector and the vector is introduced into a host to allow for production, whereby a reconstituted human antibody can be obtained (see EP125023, WO96/02576).

In the present specification, moreover, the human antibody encompasses an "artificial human antibody". The artificial human antibody can be produced by conventional gene recombinant techniques disclosed in, for example, the above-mentioned document 16 and the like.

The antibody of the present invention also includes a fusion protein wherein the aforementioned antibody and other peptide or protein are fused. The production method of a fusion protein includes linking a polynucleotide encoding the antibody of the present invention and a polynucleotide encoding other peptide or polypeptide to match the frame, introducing same into an expression vector, and allowing expression thereof in a host, and techniques known to those of ordinary skill in the art can be used. As other peptide to be fused with the antibody of the present invention, known peptides such as FLAG (Hopp, T. P. et al., BioTechnology (1988) 6, 1204-1210), 6×His consisting of six His (histidine) residues, 10×His, human c-myc fragment, VSV-GP fragment, p18HIV fragment, T7-tag, HSV-tag, E-tag, SV40T antigen fragment, lck tag, α-tubulin fragment, B-tag, Protein C fragment and the like can be used. Examples of other polypeptide to be fused with the antibody of the present invention include GST (glutathione-S-transferase), HA (influenza hemagglutinin), immunoglobulin constant region, β-galactosidase, MBP (maltose binding protein) and the like. A commercially available polynucleotide encoding such peptide or polypeptide is fused with a polynucleotide encoding the antibody of the present invention, and a fusion polynucleotide prepared thereby is expressed, whereby a fusion polypeptide can be prepared.

The antibody of the present invention may be a conjugate antibody bound with various molecules, for example, polymer substances such as polyethylene glycol (PEG), hyaluronic acid and the like, radioactive substance, fluorescent substance, luminescence substance, enzyme, toxin and the like. Such conjugate antibody can be obtained by chemically modifying the obtained antibody. The modification method of antibody has already been established in this field (e.g., U.S. Pat. Nos. 5,057,313, 5,156,840).

The antibody of the present invention is preferably isolated or purified. Being "isolated or purified" means that an operation to remove components other than the component of interest has been applied to the state of natural presence. The purity of the isolated or purified antibody of the present invention (ratio of the weight of the antibody of the present invention to the total protein weight) is generally 50% or more, preferably 70% or more, more preferably 90% or more, most preferably 95% or more (e.g., substantially 100%).

In a preferable embodiment, the antibody of the present invention binds to human ADAM28 in an epitope comprising the amino acid sequence shown in SEQ ID NO: 21, 22 or 23.

Examples of the epitope comprising the amino acid sequence shown in SEQ ID NO: 21 (ENFSKWRGS: hADAM28s 274-282) includes an epitope consisting of a continuous partial sequence of the amino acid sequence shown in SEQ ID NO: 4, which comprises the amino acid sequence shown in SEQ ID NO: 21, and preferably has an amino acid length of 20 or less, more preferably 12 or less. As the epitope comprising the amino acid sequence shown in SEQ ID NO: 21, specifically, an epitope consisting of the amino acid sequence shown in SEQ ID NO: 21, an epitope consisting of the amino acid sequence shown in SEQ ID NO: 32 (FTLENFSKWRGS), and an epitope consisting of the amino acid sequence shown in SEQ ID NO: 33 (ENFSKWRGSVLS) can be mentioned.

Examples of the epitope comprising the amino acid sequence shown in SEQ ID NO: 22 (TELWGPGRRT: hADAM28s 517-526) includes an epitope consisting of a continuous partial sequence of the amino acid sequence shown in SEQ ID NO: 4, which comprises the amino acid sequence shown in SEQ ID NO: 22, and preferably has an amino acid length of 20 or less, more preferably 12 or less. As the epitope comprising the amino acid sequence shown in SEQ ID NO: 22, specifically, an epitope consisting of the amino acid sequence shown in SEQ ID NO: 22 can be mentioned.

Examples of the epitope comprising the amino acid sequence shown in SEQ ID NO: 23 (LFNAPLPT: hADAM28s 395-402), includes an epitope consisting of a continuous partial sequence of the amino acid sequence shown in SEQ ID NO: 4, which comprises the amino acid sequence shown in SEQ ID NO: 23, and preferably has an amino acid length of 20 or less, more preferably 12 or less.

As the epitope comprising the amino acid sequence shown in SEQ ID NO: 23, specifically, an epitope consisting of the amino acid sequence shown in SEQ ID NO: 23, an epitope consisting of the amino acid sequence shown in SEQ ID NO: 34 (LSNCLFNAPLPT), and an epitope consisting of the amino acid sequence shown in SEQ ID NO: 35 (CLFNAPLPTDII) can be mentioned.

As a preferable embodiment of the antibody of the present invention, the antibodies described in the following (1)-(4) can be mentioned:

(1) an antibody comprising a light chain variable region and a heavy chain variable region,
wherein the light chain variable region comprises CDR1 comprising the amino acid sequence shown in SEQ ID NO: 5, CDR2 comprising the amino acid sequence shown in SEQ ID NO: 6 and CDR3 comprising the amino acid sequence shown in SEQ ID NO: 7, and
the heavy chain variable region comprises CDR1 comprising the amino acid sequence shown in SEQ ID NO: 8, CDR2 comprising the amino acid sequence shown in SEQ ID NO: 9 and CDR3 comprising the amino acid sequence shown in SEQ ID NO: 10;

(2) an antibody comprising a light chain variable region and a heavy chain variable region,
wherein the light chain variable region comprises CDR1 comprising the amino acid sequence shown in SEQ ID NO: 5, CDR2 comprising the amino acid sequence shown in SEQ ID NO: 6 and CDR3 comprising the amino acid sequence shown in SEQ ID NO: 7, and
the heavy chain variable region comprises CDR1 comprising the amino acid sequence shown in SEQ ID NO: 8, CDR2 comprising the amino acid sequence shown in SEQ ID NO: 9 and CDR3 comprising the amino acid sequence shown in SEQ ID NO: 10
except that 1 to 3 amino acids are substituted, deleted, inserted, and/or added in at least one amino acid sequence selected from the group consisting of the amino acid sequences shown in SEQ ID NOs: 5, 6 and 7, and/or
1 to 3 amino acids are substituted, deleted, inserted, and/or added in at least one amino acid sequence selected from the group consisting of the amino acid sequences shown in SEQ ID NOs: 8, 9 and 10.

(3) an antibody comprising a light chain variable region and a heavy chain variable region,
wherein the light chain variable region comprises CDR1 comprising the amino acid sequence shown in SEQ ID NO: 11, CDR2 comprising the amino acid sequence shown in SEQ ID NO: 12 and CDR3 comprising the amino acid sequence shown in SEQ ID NO: 13, and
the heavy chain variable region comprises CDR1 comprising the amino acid sequence shown in SEQ ID NO: 14, CDR2 comprising the amino acid sequence shown in SEQ ID NO: 15 and CDR3 comprising the amino acid sequence shown in SEQ ID NO: 16;

(4) an antibody comprising a light chain variable region and a heavy chain variable region,
wherein the light chain variable region comprises CDR1 comprising the amino acid sequence shown in SEQ ID NO: 11, CDR2 comprising the amino acid sequence shown in SEQ ID NO: 12 and CDR3 comprising the amino acid sequence shown in SEQ ID NO: 13, and
the heavy chain variable region comprises CDR1 comprising the amino acid sequence shown in SEQ ID NO: 14, CDR2 comprising the amino acid sequence shown in SEQ ID NO: 15 and CDR3 comprising the amino acid sequence shown in SEQ ID NO: 16,
except that 1 to 3 amino acids are substituted, deleted, inserted, and/or added in at least one amino acid sequence selected from the group consisting of the amino acid sequences shown in SEQ ID NOs: 11, 12 and 13, and/or
1 to 3 amino acids are substituted, deleted, inserted, and/or added in at least one amino acid sequence selected from the group consisting of the amino acid sequences shown in SEQ ID NOs: 14, 15 and 16;

(5) an antibody comprising a light chain variable region and a heavy chain variable region,
wherein the light chain variable region comprises CDR1 comprising the amino acid sequence shown in SEQ ID NO: 24, CDR2 comprising the amino acid sequence shown in SEQ ID NO: 25 and CDR3 comprising the amino acid sequence shown in SEQ ID NO: 26, and
the heavy chain variable region comprises CDR1 comprising the amino acid sequence shown in SEQ ID NO: 27, CDR2 comprising the amino acid sequence shown in SEQ ID NO: 28 and CDR3 comprising the amino acid sequence shown in SEQ ID NO: 29; and (6) an antibody comprising a light chain variable region and a heavy chain variable region,
wherein the light chain variable region comprises CDR1 comprising the amino acid sequence shown in SEQ ID NO: 24, CDR2 comprising the amino acid sequence shown in SEQ ID NO: 25 and CDR3 comprising the amino acid sequence shown in SEQ ID NO: 26, and
the heavy chain variable region comprises CDR1 comprising the amino acid sequence shown in SEQ ID NO: 27, CDR2 comprising the amino acid sequence shown in SEQ ID NO: 28 and CDR3 comprising the amino acid sequence shown in SEQ ID NO: 29,
except that 1 to 3 amino acids are substituted, deleted, inserted, and/or added in at least one amino acid sequence selected from the group consisting of the amino acid sequences shown in SEQ ID NOs: 24, 25 and 26, and/or
1 to 3 amino acids are substituted, deleted, inserted, and/or added in at least one amino acid sequence selected from the group consisting of the amino acid sequences shown in SEQ ID NOs: 27, 28 and 29.

In the embodiments of (2), (4) and (6), the number of amino acids to be substituted, deleted, inserted and/or added is not particularly limited as long as the antibody has specific binding activity to human ADAM28, and has an activity to inhibit the enzyme activity of human ADAM28. It is preferably within 2 amino acids, more preferably one amino acid, per one CDR sequence. While the number of CDR sequences in which amino acid is substituted, deleted, inserted and/or added is not particularly limited as long as the antibody has specific binding activity to human ADAM28, and has an activity to inhibit the enzyme activity of ADAM28. It is preferably within 2, more preferably one, per one light chain variable region, and preferably within 2, more preferably 1, per one heavy chain variable region. The substitution, deletion, insertion and/or addition of amino acid may be performed in both the light chain variable region and the heavy chain variable region, or either one of them.

In the embodiments of (2), (4) and (6), 1-3 (preferably 1 or 2, more preferably 1) amino acids are preferably substituted, deleted, inserted, and/or added only in the amino acid sequence of CDR3 in the light chain variable region.

Examples of the method for substituting one or plural amino acid residues with other desired amino acid include site-directed mutagenesis method (Hashimoto-Gotoh, T, Mizuno, T, Ogasahara, Y, and Nakagawa, M. (1995) An oligodeoxyribonucleotide-directed dual amber method for site-directed mutagenesis. Gene 152, 271-275; Zoller, M J, and Smith, M. (1983) Oligonucleotide-directed mutagenesis of DNA fragments cloned into M13 vectors. Methods Enzymol. 100, 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456; Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492). Using these methods, desired amino acid in an antibody can be substituted by other amino acid of interest. Also, using the library technique such as framework shuffling (Mol Immunol. 2007 April; 44(11): 3049-60) and CDR repair (US2006/0122377) and the like, an amino acid in a framework or CDR can also be substituted by other appropriate amino acid.

In the antibody of the present invention, as a framework region (FR) of the antibody to be linked to a CDR, a framework which enables the CDR to form a good antigen binding site is selected. While FR to be used for the antibody of the present invention is not particularly limited and any FRs can be used, FR of a human antibody is preferably used. As the FR of a human antibody, one having a natural sequence may be used, or one or plural amino acids in the framework region having a natural sequence may be substituted, deleted, added and/or inserted and the like as necessary, so that CDR will form an appropriate antigen binding site. For example, a mutant FR sequence having desired properties can be selected by measuring and evaluating the binding activity of an antibody having FR with substituted amino acid to an antigen (Sato, K. et al., Cancer Res. (1993)53, 851-856).

In the antibodies of (1) and (2), FR of Vk1 (Kabat database) of human antibody is preferably used for the light chain, and FR of VH5 (Kabat database) of human antibody is preferably used for the heavy chain.

In the antibodies of (3) and (4), FR of Vk2 (Kabat database) of human antibody is preferably used for the light chain, and FR of VH6 (Kabat database) of human antibody is preferably used for the heavy chain.

In the antibodies of (5) and (6), FR of Vk2 (Kabat database) of human antibody is preferably used for the light chain, and FR of VH3 (Kabat database) of human antibody is preferably used for the heavy chain.

The constant region used for the antibody of the present invention is not particularly limited, and any constant region may be used. Preferable examples of the constant region used for the antibody of the present invention include constant regions of human antibody (constant regions derived from IgG1, IgG2, IgG3, IgG4, IgA, IgM and the like). For example, Cγ1, Cγ2, Cγ3, Cγ4, Cμ, Cδ, cα1, cα2, Cε can be used in H chain, and Cκ, Cλ can be used in L chain.

In the antibodies of (1)-(4), the constant region of Cκ of human antibody is preferably used for the light chain, and the constant region of Cγ1 of human antibody is preferably used for the heavy chain.

In the antibodies of (5) and (6), the constant region of Cκ of human antibody is preferably used for the light chain, and the constant region of Cγ1 of human antibody is preferably used for the heavy chain.

Preferable antibody of the present invention includes the following:
(1') An antibody comprising a light chain variable region and a heavy chain variable region, wherein the light chain variable region comprises the amino acid sequence shown in SEQ ID NO: 17 and the heavy chain variable region comprises the amino acid sequence shown in SEQ ID NO: 18;
(3') an antibody comprising a light chain variable region and a heavy chain variable region, wherein the light chain variable region comprises the amino acid sequence shown in SEQ ID NO: 19 and the heavy chain variable region comprises the amino acid sequence shown in SEQ ID NO: 20; and
(5') an antibody comprising a light chain variable region and a heavy chain variable region, wherein the light chain variable region comprises the amino acid sequence shown in SEQ ID NO: 30 and the heavy chain variable region comprises the amino acid sequence shown in SEQ ID NO: 31.

The antibody of the above-mentioned (1') corresponds to a preferable embodiment of the antibody of the above-mentioned (1), and the antibody of the above-mentioned (3') corresponds to a preferable embodiment of the antibody of the above-mentioned (3), respectively. The antibody of the above-mentioned (5') corresponds to a preferable embodiment of the antibody of the above-mentioned (5), respectively.

The present invention provides a polynucleotide containing a nucleotide sequence encoding the above-mentioned antibody of the present invention. The polynucleotide may be a DNA or RNA, or a DNA/RNA chimera. The polynucleotide may be double stranded or single stranded. When the polynucleotide is double stranded, it may be a double stranded DNA, a double stranded RNA or a DNA:RNA hybrid.

The polynucleotide of the present invention encompasses a polynucleotide containing a nucleotide sequence encoding both the heavy chain variable region and the light chain variable region of the antibody of the present invention, and a combination of a polynucleotide containing a nucleotide sequence encoding the heavy chain variable region of the antibody of the present invention and a polynucleotide containing a nucleotide sequence encoding the light chain variable region of the antibody of the present invention.

The polynucleotide of the present invention can be easily produced based on the information of the amino acid sequence of the antibody of the present invention, known sequence information and sequence information described in the Sequence Listing in the present specification, and by utilizing known gene recombination techniques. For example, suitable primers are designed based on the sequence information, a DNA encoding the elements constituting the antibody of the present invention is amplified by the PCR reaction, DNA fragments are ligated by appropriate enzymes such as ligase and the like, whereby the polynucleotide of the present invention can be produced. Alternatively, a polynucleotide encoding each element may be synthesized by a polynucleotide synthesizer, based on the information of the amino acid sequence of the antibody of the present invention.

The obtained polynucleotide encoding the antibody of the present invention may be, depending on the object, directly used, or used after digestion with a restriction enzyme when desired, or addition of a linker. The polynucleotide may have ATG as a translation initiation codon on the 5' terminus side, and may have TAA, TGA or TAG as a translation stop codon on the 3' terminus side. These translation initiation codon and translation stop codon can be added using a suitable synthesized DNA adapter.

The polynucleotide of the present invention is preferably isolated or purified. The isolated or purified polynucleotide of the present invention has a purity (ratio of the weight of the polynucleotide of the present invention to the total polynucleotide weight) of generally 50% or more, preferably 70% or more, more preferably 90% or more, most preferably 95% or more (e.g., substantially 100%).

The present invention provides a vector comprising the above-mentioned polynucleotide of the present invention. The vector of the present invention encompasses a vector comprising a polynucleotide comprising a nucleotide sequence encoding both the heavy chain variable region and the light chain variable region of the antibody of the present invention, and a combination of a vector comprising a polynucleotide comprising a nucleotide sequence encoding the heavy chain variable region of the antibody of the present invention and a vector comprising a polynucleotide comprising a nucleotide sequence encoding the light chain variable region of the antibody of the present invention. The vector is preferably isolated or purified. Examples of the vector include expression vector, cloning vector and the like, which can be selected according to the object. Preferably, the vector is an expression vector. The expression vector can express the antibody of the present invention. The expression vector can be produced by operably linking the polynucleotide of the present invention to the downstream of a promoter in a suitable expression vector. The kind of the vector includes, for example, plasmid vector, virus vector and the like, which can be appropriately selected according to the host to be used.

As the host, the genus *Escherichia* (*Escherichia coli* etc.), the genus *Bacillus* (*Bacillus subtilis* etc.), yeast (*Saccharomyces cerevisiae* etc.), insect cell (established cell line derived from larva of *Mamestra brassicae* (*Spodoptera frugiperda* cell; Sfcell) etc.), insect (larva of *Bombyx mori* etc.), mammalian cells (rat nerve cell, monkey cell (COS-7 etc.), Chinese hamster cell (CHO cell etc.) etc.) and the like are used.

Examples of the mammal include, but are not limited to, experiment animals such as rodents such as mouse, rat, hamster and guinea pig and the like, rabbit and the like, domestic animals such as swine, bovine, goat, horse, sheep, mink and the like, companion animals such as dog, cat and the like, primates such as human, monkey, *Macaca fascicularis, Macaca mulatta*, marmoset, orangutan, chimpanzee and the like, and the like.

Examples of the plasmid vector include plasmid vectors derived from *Escherichia coli* (e.g., pBR322, pBR325, pUC12, pUC13), plasmid vectors derived from *Bacillus subtilis* (e.g., pUB110, pTP5, pC194), plasmid vectors derived from yeast (e.g., pSH19, pSH15) and the like, which can be appropriately selected according to the kind of the host to be used and the object of use.

The kind of the virus vector can be appropriately selected according to the kind of the host to be used and object of use.

For example, when an insect cell is used as a host, baculovirus vector and the like can be used. When a mammalian cell is used as a host, retrovirus vectors such as moloney murine leukemia virus vector, lentivirus vector, sindbis virus vector and the like, adenovirus vector, herpes virus vector, adeno-associated virus vector, parvovirus vector, vaccinia virus vector, sendai virus vector and the like can be used.

The promoter can be selected according to the kind of the host to be used, and one capable of initiating transcription in the host can be selected. For example, when the host is the genus *Escherichia*, trp promoter, lac promoter, T7 promoter and the like are preferable. When the host is the genus *Bacillus*, SPO1 promoter, SPO2 promoter, penP promoter and the like are preferable. When the host is yeast, PHO5 promoter, PGK promoter and the like are preferable. When the host is an insect cell, polyhedrin promoter, P10 promoter and the like are preferable. When the host is a mammalian cell, subgenomic (26S) promoter, CMV promoter, SRα promoter and the like are preferable.

The vector of the present invention may contain a signal sequence for antibody secretion. As the signal sequence for antibody secretion when it is produced in the periplasm of *Escherichia coli*, pelB signal sequence (Lei, S. P. et al J. Bacteriol. (1987) 169, 4379) may be used.

When desired, the vector of the present invention may contain enhancer, splicing signal, polyA addition signal, selection marker, SV40 replication origin (hereinafter sometimes to be abbreviated as SV40ori) and the like each in an operable manner. Examples of the selection marker include dihydrofolate reductase (hereinafter sometimes to be abbreviated as dhfr) gene [methotrexate (MTX) resistance], ampicillin resistance gene (sometimes to be abbreviated as Amp$^r$), neomycin resistance gene (sometimes to be abbreviated as Neo$^r$, G418 resistance) and the like.

By introducing the above-mentioned vector of the present invention into the above-mentioned host by gene transfer methods known per se (e.g., lipofection method, calcium phosphate method, microinjection method, proplast fusion method, electroporation method, DEAE dextran method, gene transfer method by Gene Gun etc.), a transformant with the vector introduced thereinto (transformant of the present invention) can be produced. When an expression vector is used as the vector to be introduced, the transformant can express the antibody of the present invention. The transformant of the present invention is useful for the production of the antibody of the present invention and the like.

The antibody of the present invention can be produced by culturing the transformant of the present invention by a method known per se according to the kind of the host, and isolating the antibody of the present invention from the culture. When the host is the genus *Escherichia*, the transformant is cultured in an appropriate medium such as LB medium, M9 medium and the like at generally about 15-43° C. for about 3-24 hr. When the host is the genus *Bacillus*, the transformant is cultured in an appropriate medium generally at about 30-40° C. for about 6-24 hr. When the host is yeast, the transformant is cultured in an appropriate medium such as Burkholder's medium and the like generally at about 20° C.-35° C. for about 24-72 hr. When the host is an insect cell or insect, the transformant is cultured in an appropriate medium such as Grace's Insect medium added with about 10% of bovine serum and the like generally at about 27° C. for about 3-5 days. When the host is an animal cell, the transformant is cultured in an appropriate medium such as MEM medium added with about 10% of bovine serum and the like generally at about 30° C.-40° C. for about 15-60 hr. In any culture, aeration and stirring may be performed as necessary.

As for the production method of antibody by genetic engineering, for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137 and the like can be referred to.

The separation and purification of the antibody of the present invention from a culture is not limited in any manner, and the separation and purification methods generally used for purification of antibody can be employed. For example, antibody can be separated and purified by appropriately selecting and combining chromatography column, filter, ultrafiltration, salting out, solvent precipitation, solvent extraction, distillation, immunoprecipitation, SDS-polyacrylamide gel electrophoresis, isoelectric focusing, dialysis, recrystallization and the like.

Examples of the chromatography include affinity chromatography, ion exchange chromatography, hydrophobic chromatography, gelfiltration, reversed-phase chromatography, adsorption chromatography and the like (Strategies for Protein Purification and Characterization: A Laboratory Course Manual. Ed Daniel R. Marshak et al., Cold Spring Harbor Laboratory Press, 1996). These chromatographys can be performed by using liquid phase chromatography, for example, liquid phase chromatography such as HPLC, FPLC and the like. Examples of the column to be used for affinity chromatography include protein A column and protein G column. For example, as a column using protein A, Hyper D, POROS, Sepharose FF (manufactured by GE Amersham Biosciences) and the like can be mentioned. The present invention also encompasses an antibody highly purified by these purification methods.

In addition, the present invention provides a pharmaceutical composition containing the above-mentioned antibody of the present invention as an active ingredient. The pharmaceutical composition of the present invention is useful as a prophylactic or therapeutic agent for cancer; a cancer proliferation inhibitor; a cancer metastasis inhibitor and the like. While the kind of cancer is not particularly limited as long as it can achieve the prophylactic or therapeutic effect for cancer; cancer proliferation inhibitory effect; or cancer metastasis inhibitory effect by the antibody of the present invention, hepatic cancer, colorectal cancer, renal cancer, melanoma, pancreatic cancer, thyroid cancer, gastric cancer, lung cancer (small cell lung cancer, non-small cell lung cancer), brain tumor, uterine cancer, breast cancer, multiple osteosarcoma, ovarian cancer, chronic leukemia, prostate cancer, acute lymphoblastic leukemia, germinoma, acute myeloid leukemia, malignant lymphoma, villous cancer, pediatric malignant tumor, gall bladder or bile duct cancer and the like can be mentioned. In a preferable embodiment, the cancer to be the application target of the antibody of the present invention is a cancer that expresses human ADAM28. Whether the cancer expresses human ADAM28 can be evaluated by Western blotting, RT-PCR and the like.

While not bound by theories, ADAM28 inhibits formation of IGF-1/IGFBP-3 complex by degrading IGFBP-3, and promotes cancer cell proliferation by IGF-1. The antibody of the present invention suppresses cancer cell proliferation by IGF-1 by inhibiting degradation of IGFBP-3 by ADAM28. In one embodiment, therefore, the cancer to be the application target of the antibody of the present invention is IGF-1 sensitive cancer (i.e., cancer showing IGF-1-dependent proliferation promotion). Whether or not the cancer is IGF-1 sensitive can be evaluated by analyzing the expression of IGF-1 receptor in cancer by Western blotting, RT-PCR and the like.

While not bound by theories, ADAM28 inhibits induction of apoptosis of cancer cell by von Willebrand factor (vWF) by degrading vWF. The antibody of the present invention promotes induction of apoptosis of cancer cells by vWF by inhibiting degradation of vWF by ADAM28, as a result of which it suppresses cancer proliferation and metastasis. In one embodiment, therefore, the cancer to be the application target in the present invention is vWF sensitive cancer (i.e., cancer permitting induction of apoptosis by vWF). Whether or no the cancer is vWF sensitive can be evaluated by culturing the cancer cells on a vWF-coated plate and analyzing the fragmentation of DNA by, for example, the method described in J Natl Cancer Inst 2012; 104:906-922.

When the antibody of the present invention is "contained as an active ingredient", it means that the antibody of the present invention is contained as at least one of the active ingredients, and does not limit the content thereof. The pharmaceutical composition of the present invention may contain other active ingredient(s) together with the antibody of the present invention.

The antibody of the present invention can be formulated according to a conventional method (e.g., Remington's Pharmaceutical Science, latest edition, Mark Publishing Company, Easton, U.S.A.). Where necessary, moreover, it may contain a pharmaceutically acceptable carrier and/or additive. For example, it can contain surfactant (PEG, Tween etc.), excipient, antioxidant (ascorbic acid etc.), colorant, flavor, preservative, stabilizer, buffering agent (phosphate, citrate, other organic acid etc.), chelating agent (EDTA etc.), suspending agent, isotonizing agent, binder, disintegrant, lubricant, glidant, corrigent and the like. Not being limited to these, the pharmaceutical composition of the present invention may contain other conventional carriers as appropriate. Specific examples include light anhydrous silicic acid, lactose, crystalline cellulose, mannitol, starch, carmellose calcium, carmellose sodium, hydroxypropylcellulose, hydroxypropylmethylcellulose, polyvinyl acetaldiethylaminoacetate, polyvinylpyrrolidone, gelatin, medium-chain fatty acid triglyceride, polyoxyethylene hydrogenated castor oil 60, sucrose, carboxymethylcellulose, cornstarch, inorganic salts and the like. It may also contain other low-molecular-weight polypeptide, serum albumin, gelatin and protein such as immunoglobulin and the like, as well as amino acid. When an aqueous solution for injection is formulated, the antibody of the present invention is dissolved in, for example, isotonic solution containing saline, glucose or other auxiliary agent. Examples of the auxiliary agent include D-sorbitol, D-mannose, D-mannitol, and sodium chloride, and may be used in combination with suitable solubilizing agents, for example, alcohol (ethanol etc.), polyalcohol (propylene glycol, PEG etc.), non-ionic surfactant (polysorbate80, HCO-50) and the like.

Where necessary, polypeptide may also be included in a microcapsule (microcapsules made of hydroxymethylcellulose, gelatin, poly[methylmethacrylate] and the like), or formulated as a colloid drug delivery system (liposome, albumin microsphere, microemulsion, nanoparticles and nanocapsule etc.) (see Remington's Pharmaceutical Science 16th edition &, Oslo Ed. (1980) etc.). Furthermore, a method of formulating a drug as a sustained-release medicament is also known, and applicable to polypeptide (Langer et al., J. Biomed. Mater. Res. (1981)15: 167-277; Langer, Chem. Tech. (1982)12: 98-105; U.S. Pat. No. 3,773,919; EP-A-58, 481; Sidman et al., Biopolymers (1983) 22: 547-56; EP No. 133,988). Furthermore, it is also possible to increase the liquid amount to be subcutaneously administered by adding or blending hyaluronidase to or with the present agent (e.g., WO 2004/078140 etc.).

The content of the antibody of the present invention in a pharmaceutical composition is, for example, about 0.01-100 wt %, preferably 0.1-99.9%, of the whole pharmaceutical composition.

While the pharmaceutical composition of the present invention can be administered both orally and parenterally, it is preferably administered parenterally. Specifically, it is administered to patients by injection or transdermal administration. As an example of the dosage form of injection, it can be administered systemically or topically by intravenously injection, intramuscular injection, subcutaneous injection and the like. It may also be administered to the treatment site or in the vicinity thereof by topical injection, particularly intramuscular injection. Examples of the dosage form of transdermal administration include ointment, gel, cream, plaster, patch and the like, which can be administered systemically or topically. In addition, the administration method can be appropriately selected according to the age and symptom of the patients. The dose can be selected from, for example, the range of 0.5 mg-10 mg/kg body weight as the antibody of the present invention. However, the pharmaceutical composition of the present invention is not limited by these doses.

All references cited in the present specification, including publication, patent document and the like, are hereby incorporated individually and specifically by reference, to the extent that the entireties thereof have been specifically disclosed herein.

EXAMPLE

The present invention is explained in more detail in the following by referring to Examples, which are not to be construed as limitative. Various gene manipulations in the Examples followed the method described in Molecular cloning third. ed. (Cold Spring Harbor Lab. Press, 2001).

Example 1

Preparation of Antigen and Antibody
(1) Preparation of Human ADAM28 Recombinant Protein (rhADAM28)
Full length rhADAM28 was prepared and purified by the method described in Biochem Biophys Res Commun. 2004; 315: 79-84.
(2) Biotinylation of rhADAM28
The purified rhADAM28 was biotinylated according to the standard protocol of EZ-Link NHS-PEO$_4$-Biotin (Thermo Scientific), and the concentration was determined by using BCA Protein Assay Kit (manufactured by PIERCE).

(3) Selection of Anti-human ADAM28 Human Antibody Clones By Phage Display Method The biotinylated rhADAM28 was immobilized on streptavidin-coated magnetic beads (Dynabeads MyOne Streptavidin T1 magnetic beads, manufactured by Invitrogen, 100 μl) at 4° C. for 1 hr, and washed 5 times with 1 ml PBST (PBS containing 0.05% Tween 20). Using HuCAL GOLD (manufactured by MorphoSys) for human antibody phage library, antibody selection was performed according to the method described in WO 2007/042309, WO 2006/122797 and the like. rhADAM28-immobilized beads were added to the phage library to bind an antigen-specific antibody. The magnetic beads were recovered and washed several times, and the phage was eluted from the magnetic beads. Escherichia coli cells were infected with the eluted phage and cultured at 37° C. overnight. An operation of phage-rescue from the phage-infected Escherichia coli cells followed a general method (Molecular cloning third. Ed. Cold Spring Harbor Lab. Press, 2001). The selection round described above was repeated several times to concentrate a phage presenting an antibody specific to the antigen.

(4) Screening for Anti-human ADAM28 Human Antibody by ELISA

The pool of Fab genes obtained after the concentration operation was subcloned to Escherichia coli expression vector. According to the method described in WO 2006/122797 and the like, the Fab antibody was expressed, and the antigen-specific antibody was screened for by the ELISA method. The Fab antibody was purified from a soluble fraction of Escherichia coli lysate according to the standard method of Strep-Tactin column (manufactured by IBA). In addition, the purity of the purified antibody was confirmed by SDS-PAGE, and the concentration was determined by using BCA Protein Assay Kit (manufactured by PIERCE).

(5) Analysis of Base Sequence of Anti-human ADAM28 Human Antibody Clones

The obtained 2 clones (211-12, 211-14) of Escherichia coli were cultured, and plasmids were recovered (QIAprep Spin MiniPrep kit: manufactured by QIAGEN) and used for the base sequence analysis. Table 1 shows the amino acid sequences of CDRs (complementarity determining regions) of the respective clones. The full-length amino acid sequences of the variable region of each clone are shown in SEQ ID NOs: 17-20.

TABLE 1

| light chain | LCDR1 | LCDR2 | LCDR3 |
|---|---|---|---|
| 211-12 | RASQDISSYLN (SEQ ID NO: 5) | YGVSTLQS (SEQ ID NO: 6) | LQYDSLPS (SEQ ID NO: 7) |
| 211-14 | RSSQSLLYSNGYIYLN (SEQ ID NO: 11) | YLGSNRAS (SEQ ID NO: 12) | FQYGGSPL (SEQ ID NO: 13) |
| heavy chain | HCDR1 | HCDR2 | HCDR3 |
| 211-12 | YSFTSYWIA (SEQ ID NO: 8) | IIYPSDSYTRYSPSFQG (SEQ ID NO: 9) | WSWMGRGFDN (SEQ ID NO: 10) |
| 211-14 | DSVSSNTAAWG (SEQ ID NO: 14) | VIYYRSKWYNDYAVSVKS (SEQ ID NO: 15) | YKESIPEYGFDF (SEQ ID NO: 16) |

(6) Preparation of IgG Antibody of Anti-Human ADAM28 Human Antibody Clones

Fab antibody genes of the obtained 2 clones were subcloned to construct IgG expression vectors (constant region of heavy chain was IgG1). HEK293T cells were transfected with these expression vectors according to the standard method of Lipofectamine (manufactured by Invitrogen), and the culture supernatant after culture for 72 hr was recovered. As the medium, DMEM (Sigma) supplemented with 10% Ultra Low IgG FBS (manufactured by Invitrogen) was used. From the culture supernatant, IgG antibody was purified by the standard method using rProteinA Sepharose Fast Flow (manufactured by GE healthcare). Protein after purification was confirmed to show a single band by SDS-PAGE, and the concentration was determined by using BCA Protein Assay Kit (manufactured by PIERCE).

(7) Preparation of Anti-human ADAM28 Mouse Monoclonal Antibody

Using purified rhADAM28 as an antigen, monoclonal antibodies to human ADAM28 protein were established. Five clones were first selected by ELISA using rhADAM28, and clone 297-2F3 was selected as a candidate antibody to human ADAM28. The mono-reactivity of monoclonal antibody (297-2F3) was determined by immunoblotting for recombinant human ADAM28.

Example 2

Suppressive Effect of Anti-human ADAM28 Antibodies on Human ADAM28 Enzyme Activity rhADAM28 and anti-ADAM28 antibody were incubated at the weight ratio shown in the Figure for 2 hr, IGFBP-3 (100 ng) was added and incubated at 37° C. for 24 hr, and the reaction was terminated with SDS-sample buffer containing 5 mM EDTA. Thereafter, the reaction product was applied to SDS-PAGE (10% acrylamide gel), and the level of degradation of IGFBP-3 was detected by the immunoblot method using anti-IGFBP-3 antibody (Santa Cruz Biotechnology, Inc., Santa Cruz, Calif.) (FIG. 1). Both 211-14 and 211-12 antibodies suppressed degradation of IGFBP-3 by human ADAM28.

Example 3

Figure 2:
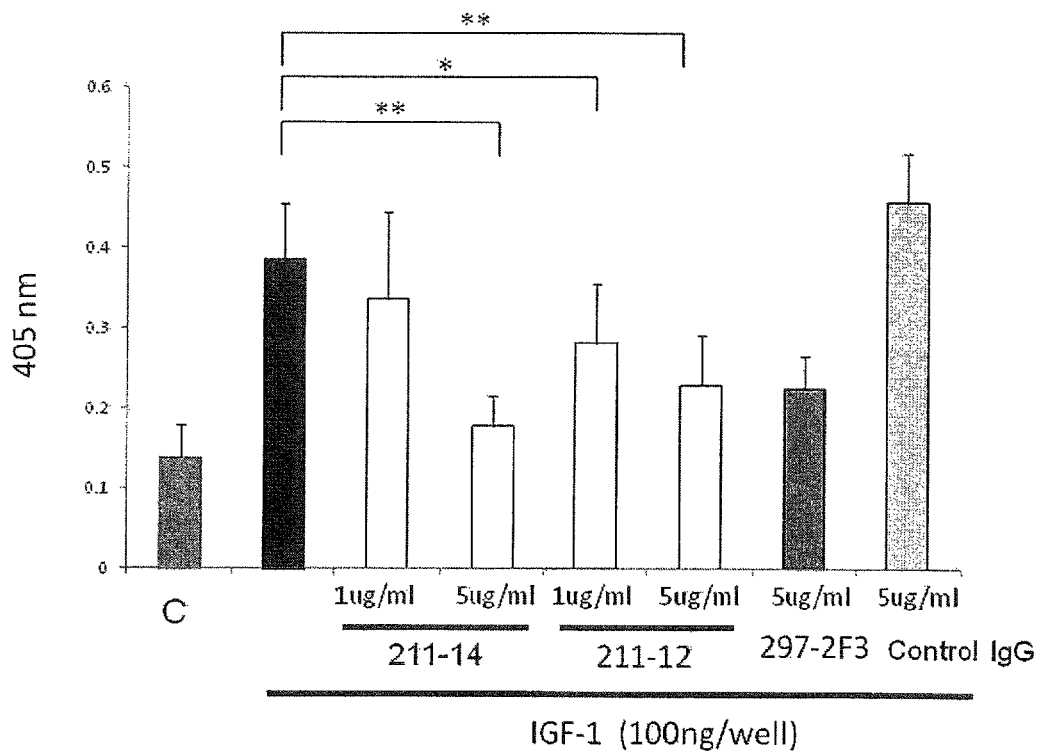
FIG. 2 shows an in vitro cancer cell proliferation inhibitory effect of anti-human ADAM28 antibody.

Proliferation Suppressive Effect of Anti-human ADAM28 Antibodies on Breast Cancer Cell Line The mitogenic effects of IGF-I on MDA-MB231 cells were measured with 5-bromo-2'deoxy-uridine (BrdUrd) Labeling and Detection Kit III (Roche Molecular Biochemicals, Basel, Switzerland) according to the instructions of the manufacturer. After synchronization and growth arrest, cells were treated with 1 µg/mL IGF-I in DMEM containing 1% FBS. After synchronization and growth arrest, cells were treated with 1 µg/mL IGF-I in DMEM containing 1% FBS. After 6 hours, BrdUrd (10 µmol/L) was added to the media and cultured for the next 42 hours. To determine the contribution of ADAM28 activity to the mitogenic effect of IGF-I, cells were incubated with 1 or 5 µg/mL anti-ADAM28 antibody 30 minutes before the IGF-I treatment, and then reacted with BrdUrd for 42 hours in the presence of IGF-I (FIG. 2). All of 211-14, 211-12 and 297-2F3 antibodies suppressed in vitro growth of MDA-MB231 cells.

Example 4

Figure 3:
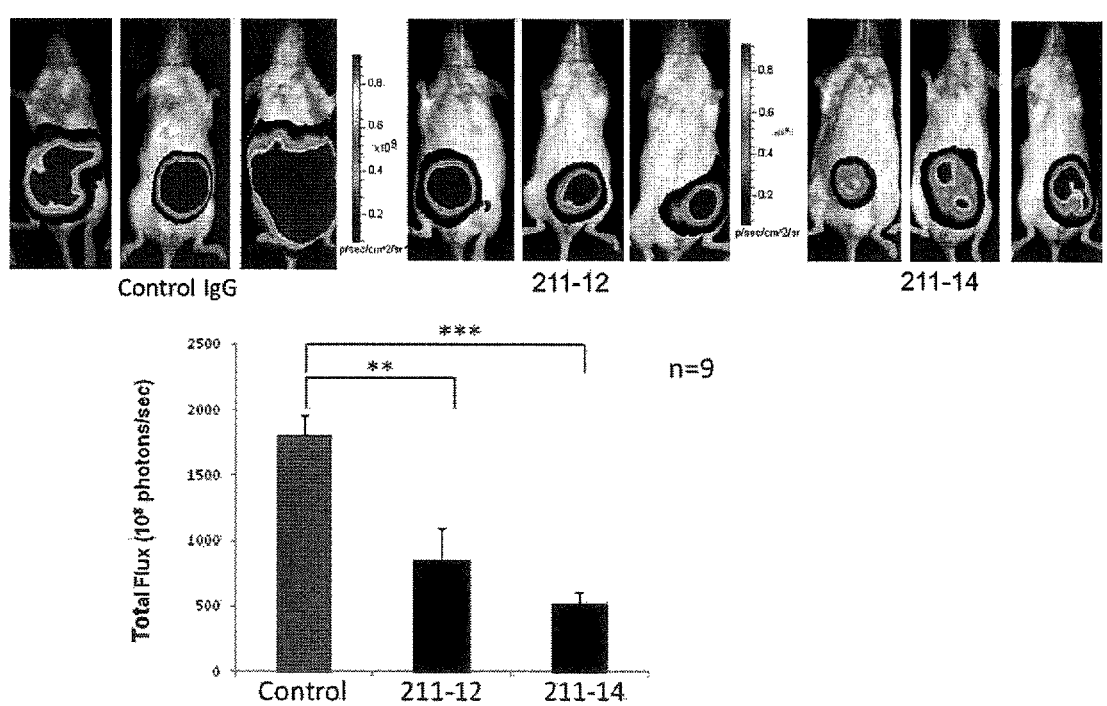
FIG. 3 shows an in vivo cancer cell proliferation inhibitory effect of anti-human ADAM28 antibody.

Suppressive Effect of Anti-human ADAM28 Antibodies on Cancer Cell Proliferation In Vivo ADAM28 high expression breast cancer cell line MDA-MB231$^{\text{\textit{ffLuc-cp156}}}$ that constitutively expresses luciferase was prepared by a lentivirus vector, and transplanted (2×10e6 cells) to a breast subcutaneous tissue of NOD/SCID mouse (Six-week-old male, Charles River Laboratories International Inc, Washington, Mass.). After transplantation, anti-ADAM28 antibody (2 mg/kg/mice) was topically injected 5 times at 2 day intervals, and the suppressive effect on tumor growth was examined. After intraperitoneal administration of D-luciferin (150 mg/Kg) (Promega Co, Madison, Mich.), the luminescence was detected by in vivo imaging system (IVIS)-100 (Xenogen Co., Alameda, Calif.) (FIG. 3). Both 211-14 and 211-12 antibodies suppressed in vivo proliferation of MDA-MB231$^{\text{\textit{ffLuc-cp156}}}$.

Example 5

Figure 4:
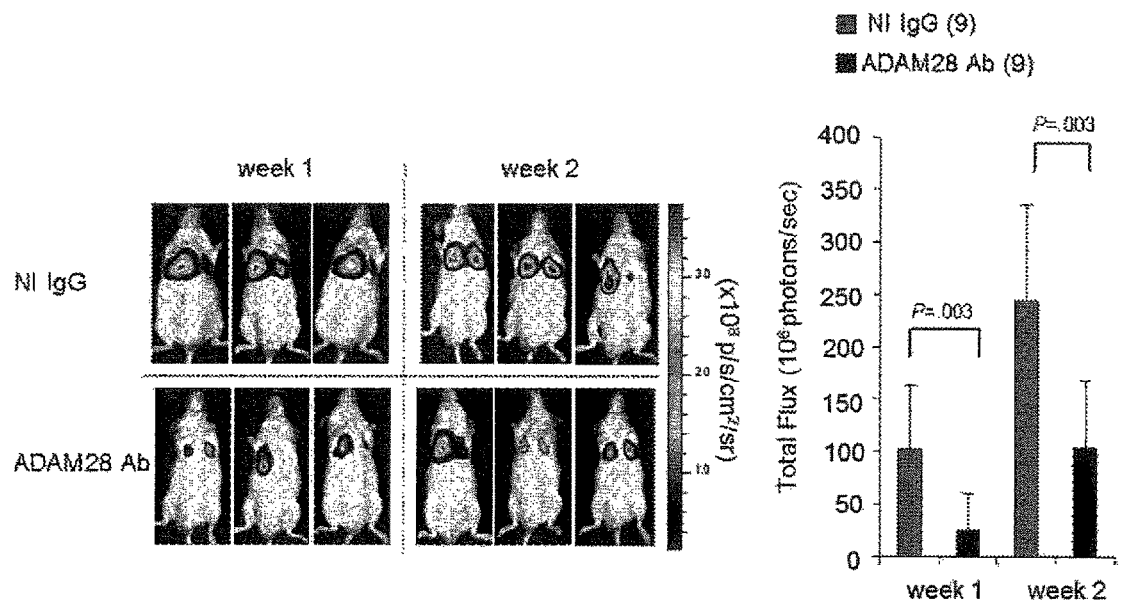
FIG. 4 shows an in vivo cancer cell metastasis inhibitory effect of anti-human ADAM28 antibody.

Suppressive Effect of Anti-human ADAM28 Antibody on Cancer Cell Metastasis In Vivo Male NOD/SCID mice (6 weeks old) (Charles River Laboratories International, Inc., Wilmington, Mass.) were injected with PC-9$^{\text{\textit{ffLuc-cp156}}}$ cells (1×10$^6$ cells in 300 µl of PBS) into the tail vein. Lung metastasis was monitored by bioluminescence imaging using the In Vivo Imaging System (IVIS)-100 camera system for detection of luciferase activity (Xenogen Co., Alameda, Calif.) according to the manufacturer's instructions. During imaging, mice were anesthetized with isoflurane and received intraperitoneal injection of D-luciferin (150 mg/kg; Promega Co., Madison, Wis.) and 1 minute later, photons from the animal whole bodies were counted. To examine the effect of neutralizing anti-ADAM28 antibody on the lung metastasis, PC-9$^{\text{\textit{ffLuc-cp156}}}$ cells were incubated with 5 µg/ml anti-human ADAM28 mouse monoclonal antibody (297-2F3) or 5 µg/ml non-immune IgG for 2 hours at 4° C. and then intravenously injected into mice (n=9 mice per each group) (FIG. 4). Cancer metastasis was suppressed by 297-2F3 administration.

Example 6

Figure 5:
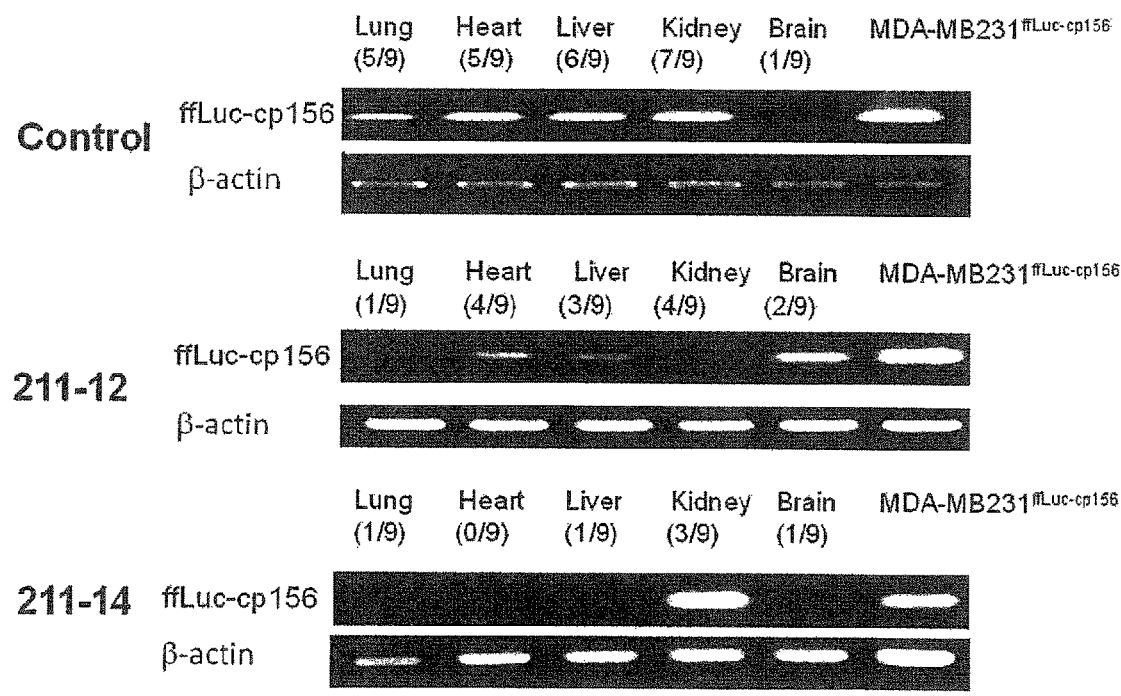
FIG. 5 shows an in vivo cancer cell metastasis inhibitory effect of anti-human ADAM28 antibody.

In Example 4, RT-PCR with luciferase specific primers was performed using RNA extracted from each organ of the mouse at 6 weeks after transplantation of cancer cells, the presence or absence of tumor-derived gene expression was confirmed, and the presence or absence of inartificial metastasis was examined (FIG. 5). Both 211-14 and 211-12 antibodies suppressed micrometastasis of cancer cells.

Example 7

With cDNA from hybridoma producing mouse anti-human ADAM28 monoclonal antibody 297-2F3, obtained in the above-mentioned Example 1(7), variable regions of the antibody were PCR-amplified, subcloned to a cloning vector, and the base sequence of the regions was analyzed. Table 2 shows the amino acid sequences of the CDRs (complementary sex determination regions). The full-length amino acid sequences of the light chain and heavy chain variable regions are respectively shown in SEQ ID NOs: 146 and 147.

TABLE 2

| light chain | LCDR1 | LCDR2 | LCDR3 |
|---|---|---|---|
| 297-2F3 | RSSQSLVLSNGNTYLN (SEQ ID NO: 24) | KISARFS (SEQ ID NO: 25) | SQTAHVPWT (SEQ ID NO: 26) |

| heavy chain | HCDR1 | HCDR2 | HCDR3 |
|---|---|---|---|
| 297-2F3 | DAWMD (SEQ ID NO: 27) | EIRSKANNHAIYYAESVKG (SEQ ID NO: 28) | FAY (SEQ ID NO: 29) |

Example 8

Then, by referring to the method described in WO 98/13388, mouse anti-human ADAM28 monoclonal antibody 297-2F3 was humanized by grafting each CDR of the antibody to a human antibody frame. The full-length amino acid sequences of the light chain and heavy chain variable regions of the thus-obtained humanized 297-2F3 are shown in SEQ ID NOs: 30 and 31, respectively.

Example 9

Identification of Epitope (1)

Using a peptide array immobilized with partial peptides of human ADAM28s, epitope mapping was performed for the anti-human ADAM28 antibodies 211-12 and 297-2F3. Specifically, as shown below, a peptide array consisting of peptides having the residue number of 12 amino acid residues with an offset of 3 amino acid residues were prepared for a sequence covering from the protease domain to the C-terminal of human ADAM28s. HRP-labeled anti-human ADAM28s antibody was reacted with the peptide array.

TABLE 3

| | | | | | | |
|---|---|---|---|---|---|---|
| 1 | VQEHEKYIEYYL (SEQ ID NO: 34) | 25 | FTLENFSKWRGS (SEQ ID NO: 58) | 49 | HNFGMFHDDYSC (SEQ ID NO: 82) | 73 | VEMGEDCDCGTS (SEQ ID NO: 106) | 97 | DDRFQVNGFPCH (SEQ ID NO: 130) |
| 2 | HEKYIEYYLVLD (SEQ ID NO: 35) | 26 | ENFSKWRGSVLS (SEQ ID NO: 59) | 50 | GMFHDDYSCKCP (SEQ ID NO: 83) | 74 | GEDCDCGTSEEC (SEQ ID NO: 107) | 98 | FQVNGFPCIIIGK (SEQ ID NO: 131) |
| 3 | YIEYYLVLDNGE (SEQ ID NO: 36) | 27 | SKWRGSVLSRRK (SEQ ID NO: 60) | 51 | HDDYSCKCPSTI (SEQ ID NO: 84) | 75 | CDCGTSEECTNI (SEQ ID NO: 108) | 99 | NGFPCIIIGKGHC (SEQ ID NO: 132) |
| 4 | YYLVLDNGEFKR (SEQ ID NO: 37) | 28 | RGSVLSRRKRHD (SEQ ID NO: 61) | 52 | YSCKCPSTICVM (SEQ ID NO: 85) | 76 | GTSEECTNICCD (SEQ ID NO: 109) | 100 | PCIIIGKGHCLMG (SEQ ID NO: 133) |
| 5 | VLDNGEFKRYNE (SEQ ID NO: 38) | 29 | VLSRRKRHDIAQ (SEQ ID NO: 62) | 53 | KCPSTICVMDKA (SEQ ID NO: 86) | 77 | EECTNICCDAKT (SEQ ID NO: 110) | 101 | HGKGHCLMGTCP (SEQ ID NO: 134) |
| 6 | NGEFKRYNENQD (SEQ ID NO: 39) | 30 | RRKRHDIAQLIT (SEQ ID NO: 63) | 54 | STICVMDKALSF (SEQ ID NO: 87) | 78 | TNICCDAKTCKI (SEQ ID NO: 111) | 102 | GHCLMGTCPTLQ (SEQ ID NO: 135) |
| 7 | FKRYNENQDEIR (SEQ ID NO: 40) | 31 | RHDIAQLITATE (SEQ ID NO: 64) | 55 | CVMDKALSFYIP (SEQ ID NO: 88) | 79 | CCDAKTCKIKAT (SEQ ID NO: 112) | 103 | LMGTCPTLQEQC (SEQ ID NO: 136) |
| 8 | YNENQDEIRKRV (SEQ ID NO: 41) | 32 | IAQLITATELAG (SEQ ID NO: 65) | 56 | DKALSFYIPTDF (SEQ ID NO: 89) | 80 | AKTCKIKATFQC (SEQ ID NO: 113) | 104 | TCPTLQEQCTEL (SEQ ID NO: 137) |
| 9 | NQDEIRKRVFEM (SEQ ID NO: 42) | 33 | LITATELAGTTV (SEQ ID NO: 66) | 57 | LSFYIPTDFSSC (SEQ ID NO: 90) | 81 | CKIKATFQCALG (SEQ ID NO: 114) | 105 | TLQEQCTELWGP (SEQ ID NO: 138) |
| 10 | EIRKRVFEMANY (SEQ ID NO: 43) | 34 | ATELAGTTVGLA (SEQ ID NO: 67) | 58 | YIPTDFSSCCRL (SEQ ID NO: 91) | 82 | KATFQCALGECC (SEQ ID NO: 115) | 106 | EQCTELWGPGRR (SEQ ID NO: 139) |
| 11 | KRVFEMANYVNM (SEQ ID NO: 44) | 35 | LAGTTVGLAFMS (SEQ ID NO: 68) | 59 | TDFSSCCRLSYD (SEQ ID NO: 92) | 83 | FQCALGECCEKC (SEQ ID NO: 116) | 107 | TELWGPGRRTNP (SEQ ID NO: 140) |
| 12 | FEMANYVNMLYK (SEQ ID NO: 45) | 36 | TTVGLAFMSTMC (SEQ ID NO: 69) | 60 | SSCCRLSYDKFF (SEQ ID NO: 93) | 84 | ALGECCEKCQFK (SEQ ID NO: 117) | 108 | WGPGRRTNPFPC (SEQ ID NO: 141) |
| 13 | ANYVNMLYKKLN (SEQ ID NO: 46) | 37 | GLAFMSTMCSPY (SEQ ID NO: 70) | 61 | SRLSYDKFFEDK (SEQ ID NO: 94) | 85 | ECCEKCQFKKAG (SEQ ID NO: 118) | 109 | GRRTNPFPCACA (SEQ ID NO: 142) |
| 14 | VNMLYKKLNTHV (SEQ ID NO: 47) | 38 | FMSTMCSPYSVG (SEQ ID NO: 71) | 62 | SYDKFFEDKLSN (SEQ ID NO: 95) | 86 | EKCQFKKAGMVC (SEQ ID NO: 119) | 110 | TNPFPCACAKEN (SEQ ID NO: 143) |
| 15 | LYKKLNTHVALV (SEQ ID NO: 48) | 39 | TMCSPYSVGVVQ (SEQ ID NO: 72) | 63 | KFFEDKLSNCLF (SEQ ID NO: 96) | 87 | QFKKAGMVCRPA (SEQ ID NO: 120) | 111 | FPCACAKENHFR (SEQ ID NO: 144) |
| 16 | KLNTHVALVGME (SEQ ID NO: 49) | 40 | SPYSVGVVQDHS (SEQ ID NO: 73) | 64 | EDKLSNCLFNAP (SEQ ID NO: 97) | 88 | KAGMVCRPAKDE (SEQ ID NO: 121) | | |
| 17 | THVALVGMEIWT (SEQ ID NO: 50) | 41 | SVGVVQDHSDNL (SEQ ID NO: 74) | 65 | LSNCLFNAPLPT (SEQ ID NO: 98) | 89 | MVCRPAKDECDL (SEQ ID NO: 122) | | |

TABLE 3-continued

| | | | | | |
|---|---|---|---|---|---|
| 18 | ALVGMEIWTDKD (SEQ ID NO: 51) | 42 | VVQDHSDNLLRV (SEQ ID NO: 75) | 66 | CLFNAPLPTDII (SEQ ID NO: 99) | 90 | RPAKDECDLPEM (SEQ ID NO: 123) |
| 19 | GMEIWTDKDKIK (SEQ ID NO: 52) | 43 | DHSDNLLRVAGT (SEQ ID NO: 76) | 67 | NAPLPTDIISTP (SEQ ID NO: 100) | 91 | KDECDLPEMCNG (SEQ ID NO: 124) |
| 20 | IWTDKDKIKITP (SEQ ID NO: 53) | 44 | DNLLRVAGTMAH (SEQ ID NO: 77) | 68 | LPTDIISTPICG (SEQ ID NO: 101) | 92 | CDLPEMCNGKSG (SEQ ID NO: 125) |
| 21 | DKDKIKITPNAS (SEQ ID NO: 54) | 45 | LRVAGTMAHEMG (SEQ ID NO: 78) | 69 | DIISTPICGNQL (SEQ ID NO: 102) | 93 | PEMCNGKSGNCP (SEQ ID NO: 126) |
| 22 | KIKITPNASFTL (SEQ ID NO: 55) | 46 | AGTMAHEMGHNF (SEQ ID NO: 79) | 70 | STPICGNQLVEM (SEQ ID NO: 103) | 94 | CNGKSGNCPDDR (SEQ ID NO: 127) |
| 23 | ITPNASFTLENF (SEQ ID NO: 56) | 47 | MAHEMGHNFGMF (SEQ ID NO: 80) | 71 | ICGNQLVEMGED (SEQ ID NO: 104) | 95 | KSGNCPDDRFQV (SEQ ID NO: 128) |
| 24 | NASFTLENFSKW (SEQ ID NO: 57) | 48 | EMGHNFGMFHDD (SEQ ID NO: 81) | 72 | NQLVEMGEDCDC (SEQ ID NO: 105) | 96 | NCPDDRFQVNGF (SEQ ID NO: 129) |

As a result, 211-12 specifically bound to the above-mentioned peptides #25 and #26. The results suggest that the epitope of 211-12 contains the amino acid sequence shown in SEQ ID NO: 21 (ENFSKWRGS) common to peptides #25 and #26.

297-2F3 specifically bound to the above-mentioned peptides #65 and #66. In the consensus amino acid sequence (CLFNAPLPT: SEQ ID NO: 145) of peptides #65 and #66, cysteine is not recognized by antibodies in most cases. Therefore, it is suggested that the epitope of 297-2F3 contains the amino acid sequence shown in SEQ ID NO: 23 (LFNAPLPT). It was confirmed that 297-2F3 specifically recognizes SEQ ID NO: 23 as an epitope by dot blot using a lysate of *Escherichia coli* forcibly expressing a fusion protein comprising the amino acid sequence shown in SEQ ID NO: 23 added to the C-terminal of MBP.

Example 9

Identification of Epitope (2)

Fusion proteins comprising a partial sequence of the following regions of human ADAM28s (SEQ ID NO: 4) added to the C-terminal of MBP were respectively prepared. 399-540, 399-497, 491-540, 491-510, 501-520, 511-530, 521-540, 513-522, 515-524, 517-526, 519-528

As a control, a fusion protein comprising a partial sequence of the following region of human ADAM28m (SEQ ID NO: 2) added to the C-terminal of MBP was prepared. 517-526 (human ADAM28m, as control)

The reactivity of anti-human ADAM28 antibody 211-14 to the above-mentioned fusion proteins was evaluated by Western blotting. As a result, 211-14 strongly bound to a fusion proteins containing a partial sequence of the regions 399-540, 491-540, 511-530 and 517-526 of human ADAM28s. The results suggest that the epitope of 211-14 contains the 517-526 region (TELWGPGRRT, SEQ ID NO: 22) of human ADAM28s.

Table 4-1
SEQ ID NO: 1
human ADAM28m cDNA sequence tcactggagaggaggcagggacagacccagcagcacccacctgagcgagaa
gagcagacaccgtgctcctggaatcacccagcatgttgcaaggtctcctgc
cagtcagtctcctcctctctgttgcagtaagtgctataaaagaactccctg
gggtgaagaagtatgaagtggtttatcctataagacttatccactgcataa
aagagaggccaaagagccagagcaacaggaacaatttgaaactgaattaaa
gtataaaatgacaattaatggaaaaattgcagtgctttatttgaaaaaaa
caagaacctccttgcaccaggctacacggaaacatattataattccactgg
aaaggagatcaccacaagcccacaaattatggatgattgttattatcaagg
acatattcttaatgaaaaggtttctgacgctagcatcagcacatgtagggg
tctaaggggctacttcagtcaggggatcaaagatactttattgaacctt
aagcccatacatcgggatggacaggagcatgcactcttcaagtataaccc
tgatgaaaagaattatgacagcacctgtgggatggatgtgtgtgtgggc
ccacgatttgcagcagaacattgccctacctgccaccaaactagtaaaatt
gaaagacaggaaggttcaggaacatgagaaatacatagaatatatttggt
cctggataatggtgagtttaaaaggtacaatgagaatcaagatgagatcag
aaagagggtatttgagatggctaattatgtcaacatgctttataaaaagct
caatactcatgtggccttagttggtatggaaatctggactgacaaggataa
gataaagataaacccaaatgcaagcttcacctggagaatttttctaaatg
gagggggagtgttctctcaagaagaaagcgtcatgatattgctcagttaat
cacagcaacagaacttgctggaacgactgtgggtcttgcatttatgtctac
aatgtgttctccttattctgttggcgttgttcaggaccacagcgataatct
tcttagagttgcagggacaatggcacatgaaatgggccacaactttggaat
gtttcatgacgactattcttgcaagtgtccttctacaatatgtgtgatgga
caaagcactgagcttctatatacccacagacttcagttcctgcagccgtct
cagctatgacaagttttttcgaagatgataactttatcaaattgcctctttaatgc
tccattgcctacagatatcatatccactccaatttgtgggaaccagttggt
ggaaatgggagaggactgtgattgtgggacatctgaggaatgtaccaatat
ttgctgtgatgctaagacatgtaaaatcaaagcaacttttcaatgtgcatt
aggagaatgttgtgaaaaatgccaatttaaaaaggctgggatggtgtgcag Table 4-2 accagcaaaagatgagtgcgacctgcctgaaatgtgtaatggtaaatctgg
taattgtcctgatgatagattccaagtcaatggcttcccttgccatcacgg
gaagggccactgcttgatggggacatgccccacactgcaggagcagtgcac
agagctgtggggaccaggaactgaggttgcagataagtcatgttacaacag
gaatgaaggtgggtcaaagtacgggtactgtcgcagagtggatgacacact
cattccctgcaaagcaaatgataccatgtgtgggaagttgttctgtcaagg
tgggtcggataaatttgccctggaaaggacggatagtgactttcctgacatg
taaaacatttgatcctgaagacacaagtcaagaaataggcatggtggccaa
tggaactaagtgtggcgataacaaggtttgcattaatgcagaatgtgtgga
tattgagaaagcctacaaatcaaccaattgctcatctaagtgcaaaggaca
tgctgtgtgtgaccatgagctccagtgtcaatgtgaggaaggatggatccc
tcccgactgcgatgactcctcagtggtcttccacttctccattgtggttgg
ggtgctgttcccaatggcggtcatttttgtggtggttgctatggtaatccg
gcaccagagctccagagaaaagcagaagaaagatcagaggccactatctac
cactggcaccaggccacacaaacagaagaggaaacccagatggtaaaggc
tgttcaacccaagagatgagtcagatgaagccccatgtgtatgatctgcc
agtagaaggcaatgagccccagcctcttttcataaagacacaaacgcact
tcccctactgttttcaaggataatccagtgtctacacctaaggactcaaa
tccaaaagcatgaagcaacagctaagcaagaactaatggctaaattatcaa
cttggaaaactggaaaatctggatggcagagaaatatactatctatctcac
cagtatttgctctcgactcaagaaggttaacattttctgattcatgttaga
ctttgaagagactaaagaaaattttcaaggaggaacatatgcctgagaacct
ttgcatgaatttaaaatttcaattatccattcttataagaaggaagatga Table 4-2 ttgtaaagaaatatctccgaagttaaaatctgtaataggaattgattcatt
ctctaatgaaaacaaaacataaaaacatcacactaatcttggaggaataag
aaaaattgtacatccattaaatgtacaattgattgcaacatcttgattgtt
ttaaccattaacttgtcaaattacaatcacagtttaagaaaatgatgtaaaa
ttctgtttttgtggatctctttcctagattagcttctgaaatcattattagc
tatatcatttgaggtttttctacaatttggtataactaagaatttaaaaatg
ttttatcatatatattttgtataattaattactggcatggttaaagtggttt
tcacttttaaatggagaaaatttcagttaaattaataggataaaccaggt
tgcgaactggtgacctgtaggccatgtttgcactgcaaatatatttggtct
gaatgatattgatattggacacatagtacttttacatgttttgaatgtatt
gctaatatttaaaaattgagagatcttgcataaacaatagattcccagctt
tgtcaga

TABLE 5

SEQ ID NO: 2
human ADAM28m amino acid sequence

MLQGLLPVSLLLSVAVSAIKELPGVKKYEVVYPIRLHPLHKREAKEPE
QQEQFETELKYKMTINGKIAVLYLKKNKNLLAPGYTETYYNSTGKEIT
TSPQIMDDCYYQGHILNEKVSDASISTCRGLRGYFSQGDQRYFIEPLS
PIHRDGQEHALFKYNPDEKNYDSTCGMDGVLWAHDLQQNIALPATKLV
KLKDRKVQEHEKYIEYYLVLDNGEFKRYNENQDEIRKRVFEMANYVNM
LYKKLNTHVALVGMEIWTDKDKIKITPNASFTLENFSKWRGSVLSRRK
RHDIAQLITATELAGTTVGLAFMSTMCSPYSVGWQDHSDNLLRVAGTM
AHEMGHNFGMFHDDYSCKCPSTICVMDKALSFYIPTDFSSCSRLSYDK
FFEDKLSNCLFNAPLPTDXISTPICGNQLVEMGEDCDCGTSEECTNIC
CDAKTCKIKATFQCALGECCEKCQFKKAGMVCRPAKDECDLPEMCNGK
SGNCPDDRFQVNGFPCHHGKGHCLMGTCPTLQEQCTELWGPGTEVADK
SCYNREGGSKYGYCRRVDDTLIPCKANDTMCGKLFCQGGSDNLPWKG
RIVTFLTCKTFDPEDTSQEIGMVANGTKCGDNKVCINAECVDIEKAYK
STNCSSKCKGHAVCDHELQCQCEEGWIPPDCDDSSWFHFSIWGVLFPM
AVIFVWAMVIRHQSSREKQKKDQRPLSTTGTRPHKQKRKPQMVKAVQP
QEMSQMKPHVYDLPVEGNEPPASFHKDTNALPPTVFKDNPVSTPKDSN
PKA

TABLE 6

SEQ ID NO: 3
human ADAM28s cDNA sequence tcactggagaggaggcagggacagacccagcagcacccacctgagcgaga
agagcagacaccgtgctcctggaatcacccagcatgttgcaaggtctcct
gccagtcagtctcctcctctctgttgcagtaagtgctataaaagaactcc
ctggggtgaagaagtatgaagtggtttatcctataagacttcatccactg
cataaaagagaggccaaagagccagagcaacaggaacaatttgaaactga
attaaagtataaaatgacaattaatggaaaaattgcagtgctttatttga
aaaaaacaagaacctccttgcaccaggctacacggaaacatattataat
tccactggaaaggagatcaccacaagcccacaaattatggatgattgtta

TABLE 6-continued

SEQ ID NO: 3
human ADAM28s cDNA sequence ttatcaaggacatattcttaatgaaaaggtttctgacgctagcatcagca
catgtaggggtctaaggggctacttcagtcagggggatcaaagatacttt
attgaacctttaagccccatacatcgggatggacaggagcatgcactctt
caagtataaccctgatgaaaagaattatgacagcacctgtgggatggatg
gtgtgttgtgggcccacgatttgcagcagaacattgccctacctgccacc
aaactagtaaaattgaaagacaggaaggttcaggaacatgagaaatacat
agaatattatttggtcctggataatggtgagtttaaaaggtacaatgaga
atcaagatgagatcagaaagagggtatttgagatggctaattatgtcaac
atgctttataaaaagctcaatactcatgtggccttagttggtatggaaat
ctggactgacaaggataagataaagataaccccaaatgcaagcttcacct
tggagaattttttctaaatggaggggggagtgttctctcaagaagaaagcgt
catgatattgctcagttaatcacagcaacagaacttgctggaacgactgt
gggtcttgcatttatgtctacaatgtgttctccttattctgttggcgttg
ttcaggaccacagcgataatcttcttagagttgcagggacaatggcacat
gaaatgggccacaactttggaatgtttcatgacgactattcttgcaagtg
tccttctacaatatgtgtgatggacaaagcactgagcttctatatcccca
cagacttcagttcctgcagccgtctcagctatgacaagttttttgaagat
aaattatcaaattgcctctttaatgctccattgcctacagatatcatatc
cactccaatttgtgggaaccagttggtggaaatgggagaggactgtgatt
gtgggacatctgaggaatgtaccaatatttgctgtgatgctaagacatgt
aaaatcaaagcaacttttcaatgtgcattaggagaatgttgtgaaaatgc
caatttaaaaaggctgggatggtgtgcagaccagcaaaagatgagtgcga
cctgcctgaaatgtgtaatggtaaatctggtaattgtcctgatgatagat
tccaagtcaatggcttcccttgccatcacgggaagggccactgcttgatg
gggacatgccccacactgcaggagcagtgcacagagctgtggggaccagg
taggaggacaaatcctttccctgtgcatgtgcgaaggaaaatcatttca
gatgacagtgtttaaccatggtcaaaggaccattctgtcctatccttctt
agaagctttgaactcaaaatcatggaaaggttttaagatttgaggttggt
tttagggttgctagatttagcaagtaaaaataaggatggccccgttaaat
tttaacttaaaattaacaagttttttgttaatttttgttttttgtctca
gcatcagtatatcccatgcaatatttgaggtgtgctcatactaaaattat
ttgtgtatctgaaattcaaattaaactgggtgtcttttctttcatctg
gcaacctactaagatcataaacccttggaaatctgtgtgtgtgcgggtg
tgtgtgtgtgtgtgtgcaggggtggcagaagtactgtgggatgggaca
gaaataa

TABLE 7

SEQ ID NO: 4
human ADAM28s amino acid sequence

MLQGLLPVSLLLSVAVSAIKELPGVKKYEVVYPIRLHPLHKREAKEPEQQ
EQFETELKYKMTINGKIAVLYLKKNKNLLAPGYTETYYNSTGKEITTSPQ
IMDDCYYQGHILNEKVSDASISTCRGLRGYFSQGDQRYFIEPLSPIHRDG
QEHALFKYNPDEKNYDSTCGMDGVLWAHDLQQNIALPATKLVKLKDRKVQ
EHEKYIEYYLVLDNGEFKRYNENQDEIRKRVFEMANYVNMLYKKLNTHVA
LVGMEIWTDKDKIKITPNASFTLENFSKWRGSVLSRRKRHDIAQLITATE
LAGTTVGLAFMSTMCSPYSVGVVQDHSDNLLRVAGTMAHEMGHNFGMFHD
DYSCKCPSTICVMDKALSFYIPTDFSSCSRLSYDKFFEDKLSNCLFNAPL
PTDIISTPICGNQLVEMGEDCDCGTSEECTNICCDAKTCKIKATFQCALG
ECCEKCQFKKAGMVCRPAKDECDLPEMCNGKSGNCPDDRFQVNGFPCHHG
KGHCLMGTCPTLQEQCTELWGPGRRTNPFPCACAKENHFR

TABLE 8

SEQ ID NO: 17
211-12 VL (kappa1)

DIQMTQSPSSLSASVGDRVTITCRASQDISSYLNWYQQKPGKAPKLLIY
GVSTLQSGVPSRFSGSGSGTDFTLTISSLQPEDFATYYCLQYDSLPSTF
GQGTKVEIKRT

TABLE 9

SEQ ID NO: 18
211-12 VH (VH5)

QVQLVQSGAEVKKPGESLKISCKGSGYSFTSYWIAWVRQMPGKGLEWM
GIIYPSDSYTRYSPSFQGQVTISADKSISTAYLQWSSLKASDTAMYYC
ARWSWMGRGFDNWGQGTLVTVSS

TABLE 10

SEQ ID NO: 19
211-14 VL (kappa2)

DIVMTQSPLSLPVTPGEPASISCRSSQSLLYSNGYIYLNWYLQKPGQSPQ
LLYLGSNRASGVPDRFSGSGSGTDFTLKISRVEAEDVGVYYCFQYGGSPL
TFGQGTKVEIKRT

TABLE 11

SEQ ID NO: 20
211-14 VH (VH6)

QVQLQQSGPGLVKPSQTLSLTCAISGDSVSSNTAAWGWIRQSPGRGLEWL
YGVIYRSKWYNDYAVSVKSRITINPDTSKNQFSLQLNSVTPEDTAVYYCA
RYKESIPEYGFDFWGQGTLVTVSS

TABLE 12

SEQ ID NO: 3
humanized 297-2F3 VL (VLk2)

DIVMTQSPLSLPVTLGQPASISCRSSQSLVLSNGNTYLNWFQQRPGQSPR
LLIYKISARFSGVPDRFSGSGSGTDFTLKISRVEAEDVGVYYCSQTAHVP
WTFGGGTKVEIKRT

TABLE 13

SEQ ID NO: 31
humanized 297-2F3 VH (VH3)

QVQLVESGGGLVKPGGSLRLSCAASGFTFSDAWMDWVRQAPGKGLEWVGE
IRSKANNHAIYYAESVKGRFTISRDDSKNTLYLQMNSLKTEDTAVYYCTG
FAYWGQGTLVTVSS

INDUSTRIAL APPLICABILITY

According to the present invention, an anti-human ADAM28 antibody applicable to the prophylaxis or treatment of cancer is provided.

This application is based on a provisional patent application No. 61/724,484 filed in U.S.A. (filing date: Nov. 9, 2012), the contents of which are incorporated in full herein.

The invention claimed is:

1. An antibody specifically binding to human ADAM28 and having an activity to inhibit enzyme activity of human ADAM28, which antibody comprises a light chain variable region and a heavy chain variable region,
wherein
the light chain variable region comprises CDR1 comprising the amino acid sequence shown in SEQ ID NO: 5, CDR2 comprising the amino acid sequence shown in SEQ ID NO: 6, and CDR3 comprising the amino acid sequence shown in SEQ ID NO: 7, and
the heavy chain variable region comprises CDR1 comprising the amino acid sequence shown in SEQ ID NO: 8, CDR2 comprising the amino acid sequence shown in SEQ ID NO: 9, and CDR3 comprising the amino acid sequence shown in SEQ ID NO: 10.

2. The antibody according to claim 1 wherein the light chain variable region comprises the amino acid sequence shown in SEQ ID NO: 17, and the heavy chain variable region comprises the amino acid sequence shown in SEQ ID NO: 18.

3. A pharmaceutical composition comprising the antibody according to claim 1.

4. The antibody according to claim 1, wherein the antibody specifically binds to human ADAM28 at an epitope comprising the amino acid sequence shown in SEQ ID NO: 21.

5. A pharmaceutical composition comprising the antibody according to claim 2.

6. A pharmaceutical composition comprising the antibody according to claim 4.

7. A method of treating ADAM28 expressing cancer in a mammal, comprising administering an effective amount of the antibody according to claim 1 to the mammal.

8. The method according to claim 7, wherein the mammal is human.

9. The method according to claim 7, wherein the light chain variable region comprises the amino acid sequence shown in SEQ ID NO: 17, and the heavy chain variable region comprises the amino acid sequence shown in SEQ ID NO: 18.

10. A method of inhibiting ADAM28 expressing cancer metastasis in a mammal, comprising administering an effective amount of the antibody according to claim 1 to the mammal.

11. The method according to claim 10, wherein the mammal is human.

12. The method according to claim 10, wherein the light chain variable region comprises the amino acid sequence shown in SEQ ID NO: 17, and the heavy chain variable region comprises the amino acid sequence shown in SEQ ID NO: 18.

13. The method according to claim 7, wherein the antibody specifically binds to human ADAM28 at an epitope comprising the amino acid sequence shown in SEQ ID NO: 21.

14. The method according to claim 10, wherein the antibody specifically binds to human ADAM28 at an epitope comprising the amino acid sequence shown in SEQ ID NO: 21.

* * * * *

SEQUENCE LISTING

<160> NUMBER OF SEQ ID NOS: 147

<210> SEQ ID NO 1
<211> LENGTH: 3220

```
<212> TYPE: DNA
<213> ORGANISM: Homo sapiens
<220> FEATURE:
<221> NAME/KEY: CDS
<222> LOCATION: (84)..(2411)

<400> SEQUENCE: 1
```

| | | |
|---|---|---|
| tcactggaga ggaggcaggg acagacccag cagcacccac ctgagcgaga agagcagaca | | 60 |
| ccgtgctcct ggaatcaccc agc atg ttg caa ggt ctc ctg cca gtc agt ctc<br>                          Met Leu Gln Gly Leu Leu Pro Val Ser Leu<br>                           1              5                    10 | | 113 |
| ctc ctc tct gtt gca gta agt gct ata aaa gaa ctc cct ggg gtg aag<br>Leu Leu Ser Val Ala Val Ser Ala Ile Lys Glu Leu Pro Gly Val Lys<br>               15                   20                   25 | | 161 |
| aag tat gaa gtg gtt tat cct ata aga ctt cat cca ctg cat aaa aga<br>Lys Tyr Glu Val Val Tyr Pro Ile Arg Leu His Pro Leu His Lys Arg<br>         30                    35                   40 | | 209 |
| gag gcc aaa gag cca gag caa cag gaa caa ttt gaa act gaa tta aag<br>Glu Ala Lys Glu Pro Glu Gln Gln Glu Gln Phe Glu Thr Glu Leu Lys<br>    45                    50                   55 | | 257 |
| tat aaa atg aca att aat gga aaa att gca gtg ctt tat ttg aaa aaa<br>Tyr Lys Met Thr Ile Asn Gly Lys Ile Ala Val Leu Tyr Leu Lys Lys<br>60                    65                    70 | | 305 |
| aac aag aac ctc ctt gca cca ggc tac acg gaa aca tat tat aat tcc<br>Asn Lys Asn Leu Leu Ala Pro Gly Tyr Thr Glu Thr Tyr Tyr Asn Ser<br>75                    80                    85                   90 | | 353 |
| act gga aag gag atc acc aca agc cca caa att atg gat gat tgt tat<br>Thr Gly Lys Glu Ile Thr Thr Ser Pro Gln Ile Met Asp Asp Cys Tyr<br>               95                   100                 105 | | 401 |
| tat caa gga cat att ctt aat gaa aag gtt tct gac gct agc atc agc<br>Tyr Gln Gly His Ile Leu Asn Glu Lys Val Ser Asp Ala Ser Ile Ser<br>         110                   115                 120 | | 449 |
| aca tgt agg ggt cta agg ggc tac ttc agt cag ggg gat caa aga tac<br>Thr Cys Arg Gly Leu Arg Gly Tyr Phe Ser Gln Gly Asp Gln Arg Tyr<br>     125                   130                 135 | | 497 |
| ttt att gaa cct tta agc ccc ata cat cgg gat gga cag gag cat gca<br>Phe Ile Glu Pro Leu Ser Pro Ile His Arg Asp Gly Gln Glu His Ala<br>140                   145                 150 | | 545 |
| ctc ttc aag tat aac cct gat gaa aag aat tat gac agc acc tgt ggg<br>Leu Phe Lys Tyr Asn Pro Asp Glu Lys Asn Tyr Asp Ser Thr Cys Gly<br>155                   160                 165                 170 | | 593 |
| atg gat ggt gtg ttg tgg gcc cac gat ttg cag cag aac att gcc cta<br>Met Asp Gly Val Leu Trp Ala His Asp Leu Gln Gln Asn Ile Ala Leu<br>                 175                 180                 185 | | 641 |
| cct gcc acc aaa cta gta aaa ttg aaa gac agg aag gtt cag gaa cat<br>Pro Ala Thr Lys Leu Val Lys Leu Lys Asp Arg Lys Val Gln Glu His<br>         190                   195                 200 | | 689 |
| gag aaa tac ata gaa tat tat ttg gtc ctg gat aat ggt gag ttt aaa<br>Glu Lys Tyr Ile Glu Tyr Tyr Leu Val Leu Asp Asn Gly Glu Phe Lys<br>     205                   210                 215 | | 737 |
| agg tac aat gag aat caa gat gag atc aga aag agg gta ttt gag atg<br>Arg Tyr Asn Glu Asn Gln Asp Glu Ile Arg Lys Arg Val Phe Glu Met<br>220                   225                 230 | | 785 |
| gct aat tat gtc aac atg ctt tat aaa aag ctc aat act cat gtg gcc<br>Ala Asn Tyr Val Asn Met Leu Tyr Lys Lys Leu Asn Thr His Val Ala<br>235                   240                 245                 250 | | 833 |
| tta gtt ggt atg gaa atc tgg act gac aag gat aag ata aag ata acc<br>Leu Val Gly Met Glu Ile Trp Thr Asp Lys Asp Lys Ile Lys Ile Thr<br>                 255                 260                 265 | | 881 |
| cca aat gca agc ttc acc ttg gag aat ttt tct aaa tgg agg ggg agt | | 929 |

-continued

| | | |
|---|---|---|
| Pro Asn Ala Ser Phe Thr Leu Glu Asn Phe Ser Lys Trp Arg Gly Ser<br>270                            275                            280 | |
| gtt ctc tca aga aga aag cgt cat gat att gct cag tta atc aca gca<br>Val Leu Ser Arg Arg Lys Arg His Asp Ile Ala Gln Leu Ile Thr Ala<br>          285                        290                        295 | 977 |
| aca gaa ctt gct gga acg act gtg ggt ctt gca ttt atg tct aca atg<br>Thr Glu Leu Ala Gly Thr Thr Val Gly Leu Ala Phe Met Ser Thr Met<br>300                          305                        310 | 1025 |
| tgt tct cct tat tct gtt ggc gtt gtt cag gac cac agc gat aat ctt<br>Cys Ser Pro Tyr Ser Val Gly Val Val Gln Asp His Ser Asp Asn Leu<br>315                          320                        325                        330 | 1073 |
| ctt aga gtt gca ggg aca atg gca cat gaa atg ggc cac aac ttt gga<br>Leu Arg Val Ala Gly Thr Met Ala His Glu Met Gly His Asn Phe Gly<br>                        335                        340                        345 | 1121 |
| atg ttt cat gac gac tat tct tgc aag tgt cct tct aca ata tgt gtg<br>Met Phe His Asp Asp Tyr Ser Cys Lys Cys Pro Ser Thr Ile Cys Val<br>                  350                        355                        360 | 1169 |
| atg gac aaa gca ctg agc ttc tat ata ccc aca gac ttc agt tcc tgc<br>Met Asp Lys Ala Leu Ser Phe Tyr Ile Pro Thr Asp Phe Ser Ser Cys<br>          365                        370                        375 | 1217 |
| agc cgt ctc agc tat gac aag ttt ttt gaa gat aaa tta tca aat tgc<br>Ser Arg Leu Ser Tyr Asp Lys Phe Phe Glu Asp Lys Leu Ser Asn Cys<br>380                          385                        390 | 1265 |
| ctc ttt aat gct cca ttg cct aca gat atc ata tcc act cca att tgt<br>Leu Phe Asn Ala Pro Leu Pro Thr Asp Ile Ile Ser Thr Pro Ile Cys<br>395                          400                        405                        410 | 1313 |
| ggg aac cag ttg gtg gaa atg gga gag gac tgt gat tgt ggg aca tct<br>Gly Asn Gln Leu Val Glu Met Gly Glu Asp Cys Asp Cys Gly Thr Ser<br>                        415                        420                        425 | 1361 |
| gag gaa tgt acc aat att tgc tgt gat gct aag aca tgt aaa atc aaa<br>Glu Glu Cys Thr Asn Ile Cys Cys Asp Ala Lys Thr Cys Lys Ile Lys<br>                  430                        435                        440 | 1409 |
| gca act ttt caa tgt gca tta gga gaa tgt tgt gaa aaa tgc caa ttt<br>Ala Thr Phe Gln Cys Ala Leu Gly Glu Cys Cys Glu Lys Cys Gln Phe<br>                        445                        450                        455 | 1457 |
| aaa aag gct ggg atg gtg tgc aga cca gca aaa gat gag tgc gac ctg<br>Lys Lys Ala Gly Met Val Cys Arg Pro Ala Lys Asp Glu Cys Asp Leu<br>460                          465                        470 | 1505 |
| cct gaa atg tgt aat ggt aaa tct ggt aat tgt cct gat gat aga ttc<br>Pro Glu Met Cys Asn Gly Lys Ser Gly Asn Cys Pro Asp Asp Arg Phe<br>475                          480                        485                        490 | 1553 |
| caa gtc aat ggc ttc cct tgc cat cac ggg aag ggc cac tgc ttg atg<br>Gln Val Asn Gly Phe Pro Cys His His Gly Lys Gly His Cys Leu Met<br>                        495                        500                        505 | 1601 |
| ggg aca tgc ccc aca ctg cag gag cag tgc aca gag ctg tgg gga cca<br>Gly Thr Cys Pro Thr Leu Gln Glu Gln Cys Thr Glu Leu Trp Gly Pro<br>                  510                        515                        520 | 1649 |
| gga act gag gtt gca gat aag tca tgt tac aac agg aat gaa ggt ggg<br>Gly Thr Glu Val Ala Asp Lys Ser Cys Tyr Asn Arg Asn Glu Gly Gly<br>                        525                        530                        535 | 1697 |
| tca aag tac ggg tac tgt cgc aga gtg gat gac aca ctc att ccc tgc<br>Ser Lys Tyr Gly Tyr Cys Arg Arg Val Asp Asp Thr Leu Ile Pro Cys<br>          540                        545                        550 | 1745 |
| aaa gca aat gat acc atg tgt ggg aag ttg ttc tgt caa ggt ggg tcg<br>Lys Ala Asn Asp Thr Met Cys Gly Lys Leu Phe Cys Gln Gly Gly Ser<br>555                          560                        565                        570 | 1793 |
| gat aat ttg ccc tgg aaa gga cgg ata gtg act ttc ctg aca tgt aaa<br>Asp Asn Leu Pro Trp Lys Gly Arg Ile Val Thr Phe Leu Thr Cys Lys<br>                        575                        580                        585 | 1841 |

```
aca ttt gat cct gaa gac aca agt caa gaa ata ggc atg gtg gcc aat    1889
Thr Phe Asp Pro Glu Asp Thr Ser Gln Glu Ile Gly Met Val Ala Asn
            590                 595                 600 gga act aag tgt ggc gat aac aag gtt tgc att aat gca gaa tgt gtg    1937
Gly Thr Lys Cys Gly Asp Asn Lys Val Cys Ile Asn Ala Glu Cys Val
        605                 610                 615 gat att gag aaa gcc tac aaa tca acc aat tgc tca tct aag tgc aaa    1985
Asp Ile Glu Lys Ala Tyr Lys Ser Thr Asn Cys Ser Ser Lys Cys Lys
    620                 625                 630 gga cat gct gtg tgt gac cat gag ctc cag tgt caa tgt gag gaa gga    2033
Gly His Ala Val Cys Asp His Glu Leu Gln Cys Gln Cys Glu Glu Gly
635                 640                 645                 650 tgg atc cct ccc gac tgc gat gac tcc tca gtg gtc ttc cac ttc tcc    2081
Trp Ile Pro Pro Asp Cys Asp Asp Ser Ser Val Val Phe His Phe Ser
                655                 660                 665 att gtg gtt ggg gtg ctg ttc cca atg gcg gtc att ttt gtg gtg gtt    2129
Ile Val Val Gly Val Leu Phe Pro Met Ala Val Ile Phe Val Val Val
            670                 675                 680 gct atg gta atc cgg cac cag agc tcc aga gaa aag cag aag aaa gat    2177
Ala Met Val Ile Arg His Gln Ser Ser Arg Glu Lys Gln Lys Lys Asp
        685                 690                 695 cag agg cca cta tct acc act ggc acc agg cca cac aaa cag aag agg    2225
Gln Arg Pro Leu Ser Thr Thr Gly Thr Arg Pro His Lys Gln Lys Arg
    700                 705                 710 aaa ccc cag atg gta aag gct gtt caa ccc caa gag atg agt cag atg    2273
Lys Pro Gln Met Val Lys Ala Val Gln Pro Gln Glu Met Ser Gln Met
715                 720                 725                 730 aag ccc cat gtg tat gat ctg cca gta gaa ggc aat gag ccc cca gcc    2321
Lys Pro His Val Tyr Asp Leu Pro Val Glu Gly Asn Glu Pro Pro Ala
                735                 740                 745 tct ttt cat aaa gac aca aac gca ctt ccc cct act gtt ttc aag gat    2369
Ser Phe His Lys Asp Thr Asn Ala Leu Pro Pro Thr Val Phe Lys Asp
            750                 755                 760 aat cca gtg tct aca cct aag gac tca aat cca aaa gca tga            2411
Asn Pro Val Ser Thr Pro Lys Asp Ser Asn Pro Lys Ala
        765                 770                 775 agcaacagct aagcaagaac taatggctaa attatcaact tggaaaactg gaaaatctgg  2471
atggcagaga aatatactat ctatctcacc agtatttgct ctcgactcaa gaaggttaac  2531
attttctgat tcatgttaga cttgaagag actaaagaaa attttcaaga ggaacatatg   2591
cctgagaacc tttgcatgaa tttaaaattt caattatcca ttcttataag aaggaagatg  2651
attgtaaaga aatatctccg aagttaaaat ctgtaatagg aattgattca ttctctaatg  2711
aaaacaaaac ataaaaacat cacactaatc ttggaggaat aagaaaaatt gtacatccat  2771
taaatgtaca attgattgca acatcttgat tgttttaacc attaacttgt caaattacaa  2831
tcacagttaa gaaaatgatg taaaattctg ttttgtggat ctctttccta gattagcttc  2891
tgaaatcatt attagctata tcatttgagg ttttctacaa tttggtataa ctaagaattt  2951
aaaaatgttt tatcatatat atttgtataa ttaattactg gcatggttaa agtggttttc  3011
actttttaaa tggagaaaat ttcagttaaa ttaataggat aaaccaggtt gcgaactggt  3071
gacctgtagg ccatgtttgc actgcaaata tatttggtct gaatgatatt gatattggac  3131
acatagtact tttacatgtt tgaatgtat tgctaatatt taaaaattga gagatcttgc    3191
ataaacaata gattcccagc tttgtcaga                                    3220

<210> SEQ ID NO 2
<211> LENGTH: 775
```

```
<212> TYPE: PRT
<213> ORGANISM: Homo sapiens

<400> SEQUENCE: 2

Met Leu Gln Gly Leu Leu Pro Val Ser Leu Leu Ser Val Ala Val
1               5                   10                  15

Ser Ala Ile Lys Glu Leu Pro Gly Val Lys Lys Tyr Glu Val Val Tyr
            20                  25                  30

Pro Ile Arg Leu His Pro Leu His Lys Arg Glu Ala Lys Glu Pro Glu
            35                  40                  45

Gln Gln Glu Gln Phe Glu Thr Glu Leu Lys Tyr Lys Met Thr Ile Asn
        50                  55                  60

Gly Lys Ile Ala Val Leu Tyr Leu Lys Lys Asn Lys Asn Leu Leu Ala
65                  70                  75                  80

Pro Gly Tyr Thr Glu Thr Tyr Tyr Asn Ser Thr Gly Lys Glu Ile Thr
                85                  90                  95

Thr Ser Pro Gln Ile Met Asp Asp Cys Tyr Tyr Gln Gly His Ile Leu
            100                 105                 110

Asn Glu Lys Val Ser Asp Ala Ser Ile Ser Thr Cys Arg Gly Leu Arg
        115                 120                 125

Gly Tyr Phe Ser Gln Gly Asp Gln Arg Tyr Phe Ile Glu Pro Leu Ser
    130                 135                 140

Pro Ile His Arg Asp Gly Gln Glu His Ala Leu Phe Lys Tyr Asn Pro
145                 150                 155                 160

Asp Glu Lys Asn Tyr Asp Ser Thr Cys Gly Met Asp Gly Val Leu Trp
                165                 170                 175

Ala His Asp Leu Gln Gln Asn Ile Ala Leu Pro Ala Thr Lys Leu Val
            180                 185                 190

Lys Leu Lys Asp Arg Lys Val Gln Glu His Glu Lys Tyr Ile Glu Tyr
        195                 200                 205

Tyr Leu Val Leu Asp Asn Gly Glu Phe Lys Arg Tyr Asn Glu Asn Gln
    210                 215                 220

Asp Glu Ile Arg Lys Arg Val Phe Glu Met Ala Asn Tyr Val Asn Met
225                 230                 235                 240

Leu Tyr Lys Lys Leu Asn Thr His Val Ala Leu Val Gly Met Glu Ile
                245                 250                 255

Trp Thr Asp Lys Asp Lys Ile Lys Ile Thr Pro Asn Ala Ser Phe Thr
            260                 265                 270

Leu Glu Asn Phe Ser Lys Trp Arg Gly Ser Val Leu Ser Arg Arg Lys
        275                 280                 285

Arg His Asp Ile Ala Gln Leu Ile Thr Ala Thr Glu Leu Ala Gly Thr
    290                 295                 300

Thr Val Gly Leu Ala Phe Met Ser Thr Met Cys Ser Pro Tyr Ser Val
305                 310                 315                 320

Gly Val Val Gln Asp His Ser Asp Asn Leu Leu Arg Val Ala Gly Thr
                325                 330                 335

Met Ala His Glu Met Gly His Asn Phe Gly Met Phe His Asp Asp Tyr
            340                 345                 350

Ser Cys Lys Cys Pro Ser Thr Ile Cys Val Met Asp Lys Ala Leu Ser
        355                 360                 365

Phe Tyr Ile Pro Thr Asp Phe Ser Ser Cys Ser Arg Leu Ser Tyr Asp
    370                 375                 380

Lys Phe Phe Glu Asp Lys Leu Ser Asn Cys Leu Phe Asn Ala Pro Leu
385                 390                 395                 400
```

```
Pro Thr Asp Ile Ile Ser Thr Pro Ile Cys Gly Asn Gln Leu Val Glu
                405                 410                 415
Met Gly Glu Asp Cys Asp Cys Gly Thr Ser Glu Glu Cys Thr Asn Ile
            420                 425                 430
Cys Cys Asp Ala Lys Thr Cys Lys Ile Lys Ala Thr Phe Gln Cys Ala
            435                 440                 445
Leu Gly Glu Cys Cys Glu Lys Cys Gln Phe Lys Lys Ala Gly Met Val
        450                 455                 460
Cys Arg Pro Ala Lys Asp Glu Cys Asp Leu Pro Glu Met Cys Asn Gly
465                 470                 475                 480
Lys Ser Gly Asn Cys Pro Asp Asp Arg Phe Gln Val Asn Gly Phe Pro
                485                 490                 495
Cys His His Gly Lys Gly His Cys Leu Met Gly Thr Cys Pro Thr Leu
            500                 505                 510
Gln Glu Gln Cys Thr Glu Leu Trp Gly Pro Gly Thr Glu Val Ala Asp
            515                 520                 525
Lys Ser Cys Tyr Asn Arg Asn Glu Gly Gly Ser Lys Tyr Gly Tyr Cys
        530                 535                 540
Arg Arg Val Asp Asp Thr Leu Ile Pro Cys Lys Ala Asn Asp Thr Met
545                 550                 555                 560
Cys Gly Lys Leu Phe Cys Gln Gly Gly Ser Asp Asn Leu Pro Trp Lys
                565                 570                 575
Gly Arg Ile Val Thr Phe Leu Thr Cys Lys Thr Phe Asp Pro Glu Asp
            580                 585                 590
Thr Ser Gln Glu Ile Gly Met Val Ala Asn Gly Thr Lys Cys Gly Asp
            595                 600                 605
Asn Lys Val Cys Ile Asn Ala Glu Cys Val Asp Ile Glu Lys Ala Tyr
        610                 615                 620
Lys Ser Thr Asn Cys Ser Ser Lys Cys Lys Gly His Ala Val Cys Asp
625                 630                 635                 640
His Glu Leu Gln Cys Gln Cys Glu Glu Gly Trp Ile Pro Pro Asp Cys
                645                 650                 655
Asp Asp Ser Ser Val Val Phe His Phe Ser Ile Val Val Gly Val Leu
            660                 665                 670
Phe Pro Met Ala Val Ile Phe Val Val Ala Met Val Ile Arg His
            675                 680                 685
Gln Ser Ser Arg Glu Lys Gln Lys Lys Asp Gln Arg Pro Leu Ser Thr
        690                 695                 700
Thr Gly Thr Arg Pro His Lys Gln Lys Arg Lys Pro Gln Met Val Lys
705                 710                 715                 720
Ala Val Gln Pro Gln Glu Met Ser Gln Met Lys Pro His Val Tyr Asp
                725                 730                 735
Leu Pro Val Glu Gly Asn Glu Pro Ala Ser Phe His Lys Asp Thr
            740                 745                 750
Asn Ala Leu Pro Pro Thr Val Phe Lys Asp Asn Pro Val Ser Thr Pro
        755                 760                 765
Lys Asp Ser Asn Pro Lys Ala
    770                 775

<210> SEQ ID NO 3
<211> LENGTH: 2108
<212> TYPE: DNA
<213> ORGANISM: Homo sapiens
<220> FEATURE:
```

```
<221> NAME/KEY: CDS
<222> LOCATION: (84)..(1706)

<400> SEQUENCE: 3
tcactggaga ggaggcaggg acagacccag cagcacccac ctgagcgaga agagcagaca     60
ccgtgctcct ggaatcaccc agc atg ttg caa ggt ctc ctg cca gtc agt ctc    113
                        Met Leu Gln Gly Leu Leu Pro Val Ser Leu
                         1               5                  10 ctc ctc tct gtt gca gta agt gct ata aaa gaa ctc cct ggg gtg aag      161
Leu Leu Ser Val Ala Val Ser Ala Ile Lys Glu Leu Pro Gly Val Lys
             15                  20                  25 aag tat gaa gtg gtt tat cct ata aga ctt cat cca ctg cat aaa aga      209
Lys Tyr Glu Val Val Tyr Pro Ile Arg Leu His Pro Leu His Lys Arg
         30                  35                  40 gag gcc aaa gag cca gag caa cag gaa caa ttt gaa act gaa tta aag      257
Glu Ala Lys Glu Pro Glu Gln Gln Glu Gln Phe Glu Thr Glu Leu Lys
     45                  50                  55 tat aaa atg aca att aat gga aaa att gca gtg ctt tat ttg aaa aaa     305
Tyr Lys Met Thr Ile Asn Gly Lys Ile Ala Val Leu Tyr Leu Lys Lys
 60                  65                  70 aac aag aac ctc ctt gca cca ggc tac acg gaa aca tat tat aat tcc     353
Asn Lys Asn Leu Leu Ala Pro Gly Tyr Thr Glu Thr Tyr Tyr Asn Ser
 75                  80                  85                  90 act gga aag gag atc acc aca agc cca caa att atg gat gat tgt tat     401
Thr Gly Lys Glu Ile Thr Thr Ser Pro Gln Ile Met Asp Asp Cys Tyr
                 95                 100                 105 tat caa gga cat att ctt aat gaa aag gtt tct gac gct agc atc agc     449
Tyr Gln Gly His Ile Leu Asn Glu Lys Val Ser Asp Ala Ser Ile Ser
             110                 115                 120 aca tgt agg ggt cta agg ggc tac ttc agt cag ggg gat caa aga tac     497
Thr Cys Arg Gly Leu Arg Gly Tyr Phe Ser Gln Gly Asp Gln Arg Tyr
         125                 130                 135 ttt att gaa cct tta agc ccc ata cat cgg gat gga cag gag cat gca     545
Phe Ile Glu Pro Leu Ser Pro Ile His Arg Asp Gly Gln Glu His Ala
     140                 145                 150 ctc ttc aag tat aac cct gat gaa aag aat tat gac agc acc tgt ggg     593
Leu Phe Lys Tyr Asn Pro Asp Glu Lys Asn Tyr Asp Ser Thr Cys Gly
155                 160                 165                 170 atg gat ggt gtg ttg tgg gcc cac gat ttg cag cag aac att gcc cta     641
Met Asp Gly Val Leu Trp Ala His Asp Leu Gln Gln Asn Ile Ala Leu
                175                 180                 185 cct gcc acc aaa cta gta aaa ttg aaa gac agg aag gtt cag gaa cat     689
Pro Ala Thr Lys Leu Val Lys Leu Lys Asp Arg Lys Val Gln Glu His
            190                 195                 200 gag aaa tac ata gaa tat tat ttg gtc ctg gat aat ggt gag ttt aaa     737
Glu Lys Tyr Ile Glu Tyr Tyr Leu Val Leu Asp Asn Gly Glu Phe Lys
        205                 210                 215 agg tac aat gag aat caa gat gag atc aga aag agg gta ttt gag atg     785
Arg Tyr Asn Glu Asn Gln Asp Glu Ile Arg Lys Arg Val Phe Glu Met
Arg Tyr Asn Glu Asn Gln Asp Glu Ile Arg Lys Arg Val Phe Glu Met
    220                 225                 230 gct aat tat gtc aac atg ctt tat aaa aag ctc aat act cat gtg gcc     833
Ala Asn Tyr Val Asn Met Leu Tyr Lys Lys Leu Asn Thr His Val Ala
235                 240                 245                 250 tta gtt ggt atg gaa atc tgg act gac aag gat aag ata aag ata acc     881
Leu Val Gly Met Glu Ile Trp Thr Asp Lys Asp Lys Ile Lys Ile Thr
                255                 260                 265 cca aat gca agc ttc acc ttg gag aat ttt tct aaa tgg agg ggg agt     929
Pro Asn Ala Ser Phe Thr Leu Glu Asn Phe Ser Lys Trp Arg Gly Ser
            270                 275                 280
```

```
gtt ctc tca aga aga aag cgt cat gat att gct cag tta atc aca gca    977
Val Leu Ser Arg Arg Lys Arg His Asp Ile Ala Gln Leu Ile Thr Ala
        285             290             295 aca gaa ctt gct gga acg act gtg ggt ctt gca ttt atg tct aca atg   1025
Thr Glu Leu Ala Gly Thr Thr Val Gly Leu Ala Phe Met Ser Thr Met
300             305             310 tgt tct cct tat tct gtt ggc gtt gtt cag gac cac agc gat aat ctt   1073
Cys Ser Pro Tyr Ser Val Gly Val Val Gln Asp His Ser Asp Asn Leu
315             320             325             330 ctt aga gtt gca ggg aca atg gca cat gaa atg ggc cac aac ttt gga   1121
Leu Arg Val Ala Gly Thr Met Ala His Glu Met Gly His Asn Phe Gly
            335             340             345 atg ttt cat gac gac tat tct tgc aag tgt cct tct aca ata tgt gtg   1169
Met Phe His Asp Asp Tyr Ser Cys Lys Cys Pro Ser Thr Ile Cys Val
        350             355             360 atg gac aaa gca ctg agc ttc tat ata ccc aca gac ttc agt tcc tgc   1217
Met Asp Lys Ala Leu Ser Phe Tyr Ile Pro Thr Asp Phe Ser Ser Cys
            365             370             375 agc cgt ctc agc tat gac aag ttt ttt gaa gat aaa tta tca aat tgc   1265
Ser Arg Leu Ser Tyr Asp Lys Phe Phe Glu Asp Lys Leu Ser Asn Cys
380             385             390 ctc ttt aat gct cca ttg cct aca gat atc ata tcc act cca att tgt   1313
Leu Phe Asn Ala Pro Leu Pro Thr Asp Ile Ile Ser Thr Pro Ile Cys
395             400             405             410 ggg aac cag ttg gtg gaa atg gga gag gac tgt gat tgt ggg aca tct   1361
Gly Asn Gln Leu Val Glu Met Gly Glu Asp Cys Asp Cys Gly Thr Ser
            415             420             425 gag gaa tgt acc aat att tgc tgt gat gct aag aca tgt aaa atc aaa   1409
Glu Glu Cys Thr Asn Ile Cys Cys Asp Ala Lys Thr Cys Lys Ile Lys
        430             435             440 gca act ttt caa tgt gca tta gga gaa tgt tgt gaa aaa tgc caa ttt   1457
Ala Thr Phe Gln Cys Ala Leu Gly Glu Cys Cys Glu Lys Cys Gln Phe
            445             450             455 aaa aag gct ggg atg gtg tgc aga cca gca aaa gat gag tgc gac ctg   1505
Lys Lys Ala Gly Met Val Cys Arg Pro Ala Lys Asp Glu Cys Asp Leu
460             465             470 cct gaa atg tgt aat ggt aaa tct ggt aat tgt cct gat gat aga ttc   1553
Pro Glu Met Cys Asn Gly Lys Ser Gly Asn Cys Pro Asp Asp Arg Phe
475             480             485             490 caa gtc aat ggc ttc cct tgc cat cac ggg aag ggc cac tgc ttg atg   1601
Gln Val Asn Gly Phe Pro Cys His His Gly Lys Gly His Cys Leu Met
            495             500             505 ggg aca tgc ccc aca ctg cag gag cag tgc aca gag ctg tgg gga cca   1649
Gly Thr Cys Pro Thr Leu Gln Glu Gln Cys Thr Glu Leu Trp Gly Pro
        510             515             520 ggt agg agg aca aat cct ttc ccc tgt gca tgt gcg aag gaa aat cat   1697
Gly Arg Arg Thr Asn Pro Phe Pro Cys Ala Cys Ala Lys Glu Asn His
            525             530             535 ttc aga tga cagtgtttaa ccatggtcaa aggaccattc tgtcctatcc           1746
Phe Arg
    540 ttcttagaag ctttgaactc aaaatcatgg aaaggtttta agatttgagg ttggttttag   1806 ggttgctaga tttagcaagt aaaaataagg atggccccgt taaattttaa cttaaaatta   1866 acaagttttt tgttaatttt ttgttttttg tctcagcatc agtatatccc atgcaatatt   1926 tgaggtgtgc tcatactaaa attatttgtg tatctgaaat tcaaattaaa ctgggtgtct   1986 ttttcttttc atctgcaac cctactaaga tcataaaccc ttggaaatct gtgtgtgtgc   2046 gggtgtgtgt gtgtgtgtgt gtgcaggggt ggcagaagta ctgtgggatg ggacagaaat   2106
``` aa    2108

<210> SEQ ID NO 4
<211> LENGTH: 540
<212> TYPE: PRT
<213> ORGANISM: Homo sapiens

<400> SEQUENCE: 4

Met Leu Gln Gly Leu Leu Pro Val Ser Leu Leu Ser Val Ala Val
1               5                   10                  15

Ser Ala Ile Lys Glu Leu Pro Gly Val Lys Lys Tyr Glu Val Tyr
                20                  25                  30

Pro Ile Arg Leu His Pro Leu His Lys Arg Glu Ala Lys Glu Pro Glu
                35                  40                  45

Gln Gln Glu Gln Phe Glu Thr Glu Leu Lys Tyr Lys Met Thr Ile Asn
50                  55                  60

Gly Lys Ile Ala Val Leu Tyr Leu Lys Lys Asn Lys Asn Leu Leu Ala
65                  70                  75                  80

Pro Gly Tyr Thr Glu Thr Tyr Tyr Asn Ser Thr Gly Lys Glu Ile Thr
                85                  90                  95

Thr Ser Pro Gln Ile Met Asp Asp Cys Tyr Tyr Gln Gly His Ile Leu
                100                 105                 110

Asn Glu Lys Val Ser Asp Ala Ser Ile Ser Thr Cys Arg Gly Leu Arg
            115                 120                 125

Gly Tyr Phe Ser Gln Gly Asp Gln Arg Tyr Phe Ile Glu Pro Leu Ser
        130                 135                 140

Pro Ile His Arg Asp Gly Gln Glu His Ala Leu Phe Lys Tyr Asn Pro
145                 150                 155                 160

Asp Glu Lys Asn Tyr Asp Ser Thr Cys Gly Met Asp Gly Val Leu Trp
                165                 170                 175

Ala His Asp Leu Gln Gln Asn Ile Ala Leu Pro Ala Thr Lys Leu Val
                180                 185                 190

Lys Leu Lys Asp Arg Lys Val Gln Glu His Glu Lys Tyr Ile Glu Tyr
            195                 200                 205

Tyr Leu Val Leu Asp Asn Gly Glu Phe Lys Arg Tyr Asn Glu Asn Gln
        210                 215                 220

Asp Glu Ile Arg Lys Arg Val Phe Glu Met Ala Asn Tyr Val Asn Met
225                 230                 235                 240

Leu Tyr Lys Lys Leu Asn Thr His Val Ala Leu Val Gly Met Glu Ile
                245                 250                 255

Trp Thr Asp Lys Asp Lys Ile Lys Ile Thr Pro Asn Ala Ser Phe Thr
                260                 265                 270

Leu Glu Asn Phe Ser Lys Trp Arg Gly Ser Val Leu Ser Arg Arg Lys
            275                 280                 285

Arg His Asp Ile Ala Gln Leu Ile Thr Ala Thr Glu Leu Ala Gly Thr
        290                 295                 300

Thr Val Gly Leu Ala Phe Met Ser Thr Met Cys Ser Pro Tyr Ser Val
305                 310                 315                 320

Gly Val Val Gln Asp His Ser Asp Asn Leu Leu Arg Val Ala Gly Thr
                325                 330                 335

Met Ala His Glu Met Gly His Asn Phe Gly Met Phe His Asp Asp Tyr
                340                 345                 350

Ser Cys Lys Cys Pro Ser Thr Ile Cys Val Met Asp Lys Ala Leu Ser
            355                 360                 365

```
Phe Tyr Ile Pro Thr Asp Phe Ser Ser Cys Ser Arg Leu Ser Tyr Asp
         370                 375                 380

Lys Phe Phe Glu Asp Lys Leu Ser Asn Cys Leu Phe Asn Ala Pro Leu
385                 390                 395                 400

Pro Thr Asp Ile Ile Ser Thr Pro Ile Cys Gly Asn Gln Leu Val Glu
                 405                 410                 415

Met Gly Glu Asp Cys Asp Cys Gly Thr Ser Glu Glu Cys Thr Asn Ile
             420                 425                 430

Cys Cys Asp Ala Lys Thr Cys Lys Ile Lys Ala Thr Phe Gln Cys Ala
         435                 440                 445

Leu Gly Glu Cys Cys Glu Lys Cys Gln Phe Lys Lys Ala Gly Met Val
     450                 455                 460

Cys Arg Pro Ala Lys Asp Glu Cys Asp Leu Pro Glu Met Cys Asn Gly
465                 470                 475                 480

Lys Ser Gly Asn Cys Pro Asp Asp Arg Phe Gln Val Asn Gly Phe Pro
                 485                 490                 495

Cys His His Gly Lys Gly His Cys Leu Met Gly Thr Cys Pro Thr Leu
             500                 505                 510

Gln Glu Gln Cys Thr Glu Leu Trp Gly Pro Gly Arg Arg Thr Asn Pro
         515                 520                 525

Phe Pro Cys Ala Cys Ala Lys Glu Asn His Phe Arg
530                 535                 540

<210> SEQ ID NO 5
<211> LENGTH: 11
<212> TYPE: PRT
<213> ORGANISM: Artificial Sequence
<220> FEATURE:
<223> OTHER INFORMATION: Synthetic 211-12 LCDR1

<400> SEQUENCE: 5

Arg Ala Ser Gln Asp Ile Ser Ser Tyr Leu Asn
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic 211-12 LCDR2

<400> SEQUENCE: 6

Tyr Gly Val Ser Thr Leu Gln Ser
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic 211-12 LCDR3

<400> SEQUENCE: 7

Leu Gln Tyr Asp Ser Leu Pro Ser
1               5

<210> SEQ ID NO 8
<211> LENGTH: 9
<212> TYPE: PRT
<213> ORGANISM: Artificial Sequence
<220> FEATURE:
```

<223> OTHER INFORMATION: Synthetic 211-12 HCDR1

<400> SEQUENCE: 8

Tyr Ser Phe Thr Ser Tyr Trp Ile Ala
1               5

<210> SEQ ID NO 9
<211> LENGTH: 17
<212> TYPE: PRT
<213> ORGANISM: Artificial Sequence
<220> FEATURE:
<223> OTHER INFORMATION: Synthetic 211-12 HCDR2

<400> SEQUENCE: 9

Ile Ile Tyr Pro Ser Asp Ser Tyr Thr Arg Tyr Ser Pro Ser Phe Gln
1               5                   10                  15
Gly

<210> SEQ ID NO 10
<211> LENGTH: 10
<212> TYPE: PRT
<213> ORGANISM: Artificial Sequence
<220> FEATURE:
<223> OTHER INFORMATION: Synthetic 211-12 HCDR3

<400> SEQUENCE: 10

Trp Ser Trp Met Gly Arg Gly Phe Asp Asn
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Synthetic 211-14 LCDR1

<400> SEQUENCE: 11

Arg Ser Ser Gln Ser Leu Leu Tyr Ser Asn Gly Tyr Ile Tyr Leu Asn
1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: Synthetic 211-14 LCDR2

<400> SEQUENCE: 12

Tyr Leu Gly Ser Asn Arg Ala Ser
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic 211-14 LCDR3

<400> SEQUENCE: 13

Phe Gln Tyr Gly Gly Ser Pro Leu
1               5

<210> SEQ ID NO 14
<211> LENGTH: 11
<212> TYPE: PRT
<213> ORGANISM: Artificial Sequence

```
<220> FEATURE:
<223> OTHER INFORMATION: Synthetic 211-14 HCDR1

<400> SEQUENCE: 14

Asp Ser Val Ser Ser Asn Thr Ala Ala Trp Gly
1               5                   10

<210> SEQ ID NO 15
<211> LENGTH: 18
<212> TYPE: PRT
<213> ORGANISM: Artificial Sequence
<220> FEATURE:
<223> OTHER INFORMATION: Synthetic 211-14 HCDR2

<400> SEQUENCE: 15

Val Ile Tyr Tyr Arg Ser Lys Trp Tyr Asn Asp Tyr Ala Val Ser Val
1               5                   10                  15

Lys Ser

<210> SEQ ID NO 16
<211> LENGTH: 12
<212> TYPE: PRT
<213> ORGANISM: Artificial Sequence
<220> FEATURE:
<223> OTHER INFORMATION: Synthetic 211-14 HCDR3

<400> SEQUENCE: 16

Tyr Lys Glu Ser Ile Pro Glu Tyr Gly Phe Asp Phe
1               5                   10

<210> SEQ ID NO 17
<211> LENGTH: 109
<212> TYPE: PRT
<213> ORGANISM: Artificial Sequence
<220> FEATURE:
<223> OTHER INFORMATION: Synthetic 211-12 VL

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Val Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Ser Leu Pro Ser
                85                  90                  95

Thr Phe Gly Gln Gly Thr Lys Val Glu Ile Lys Arg Thr
            100                 105

<210> SEQ ID NO 18
<211> LENGTH: 119
<212> TYPE: PRT
<213> ORGANISM: Artificial Sequence
<220> FEATURE:
<223> OTHER INFORMATION: Synthetic 211-12 VH

<400> SEQUENCE: 18

Gln Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Thr Ser Tyr
             20                  25                  30

Trp Ile Ala Trp Val Arg Gln Met Pro Gly Lys Gly Leu Glu Trp Met
         35                  40                  45

Gly Ile Ile Tyr Pro Ser Asp Ser Tyr Thr Arg Tyr Ser Pro Ser Phe
     50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                 85                  90                  95

Ala Arg Trp Ser Trp Met Gly Arg Gly Phe Asp Asn Trp Gly Gln Gly
            100                 105                 110

Thr Leu Val Thr Val Ser Ser
            115
```

<210> SEQ ID NO 19
<211> LENGTH: 114
<212> TYPE: PRT
<213> ORGANISM: Artificial Sequence
<220> FEATURE:
<223> OTHER INFORMATION: Synthetic 211-14 VL

<400> SEQUENCE: 19

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
             20                  25                  30

Asn Gly Tyr Ile Tyr Leu Asn Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Tyr
                 85                  90                  95

Gly Gly Ser Pro Leu Thr Phe Gly Gln Gly Thr Lys Val Glu Ile Lys
            100                 105                 110

Arg Thr
```

<210> SEQ ID NO 20
<211> LENGTH: 124
<212> TYPE: PRT
<213> ORGANISM: Artificial Sequence
<220> FEATURE:
<223> OTHER INFORMATION: Synthetic 211-14 VH

<400> SEQUENCE: 20

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
             20                  25                  30

Thr Ala Ala Trp Gly Trp Ile Arg Gln Ser Pro Gly Arg Gly Leu Glu
         35                  40                  45

Trp Leu Gly Val Ile Tyr Tyr Arg Ser Lys Trp Tyr Asn Asp Tyr Ala
     50                  55                  60

Val Ser Val Lys Ser Arg Ile Thr Ile Asn Pro Asp Thr Ser Lys Asn
65                  70                  75                  80
```

```
Gln Phe Ser Leu Gln Leu Asn Ser Val Thr Pro Glu Asp Thr Ala Val
                85                  90                  95
Tyr Tyr Cys Ala Arg Tyr Lys Glu Ser Ile Pro Glu Tyr Gly Phe Asp
            100                 105                 110
Phe Trp Gly Gln Gly Thr Leu Val Thr Val Ser Ser
        115                 120
```

```
<210> SEQ ID NO 21
<211> LENGTH: 9
<212> TYPE: PRT
<213> ORGANISM: Artificial Sequence
<220> FEATURE:
<223> OTHER INFORMATION: Synthetic 211-12 epitope

<400> SEQUENCE: 21

Glu Asn Phe Ser Lys Trp Arg Gly Ser
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic 211-14 epitope

<400> SEQUENCE: 22

Thr Glu Leu Trp Gly Pro Gly Arg Arg Thr
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Synthetic 297-2F3 epitope

<400> SEQUENCE: 23

Leu Phe Asn Ala Pro Leu Pro Thr
1               5

<210> SEQ ID NO 24
<211> LENGTH: 16
<212> TYPE: PRT
<213> ORGANISM: Artificial Sequence
<220> FEATURE:
<223> OTHER INFORMATION: Synthetic 297-2F3 LCDR1

<400> SEQUENCE: 24

Arg Ser Ser Gln Ser Leu Val Leu Ser Asn Gly Asn Thr Tyr Leu Asn
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Synthetic 297-2F3 LCDR2

<400> SEQUENCE: 25

Lys Ile Ser Ala Arg Phe Ser
1               5

<210> SEQ ID NO 26
<211> LENGTH: 9
<212> TYPE: PRT
```

```
<213> ORGANISM: Artificial Sequence
<220> FEATURE:
<223> OTHER INFORMATION: Synthetic 297-2F3 LCDR3

<400> SEQUENCE: 26

Ser Gln Thr Ala His Val Pro Trp Thr
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic 297-2F3 HCDR1

<400> SEQUENCE: 27

Asp Ala Trp Met Asp
1               5

<210> SEQ ID NO 28
<211> LENGTH: 19
<212> TYPE: PRT
<213> ORGANISM: Artificial Sequence
<220> FEATURE:
<223> OTHER INFORMATION: Synthetic 297-2F3 HCDR2

<400> SEQUENCE: 28

Glu Ile Arg Ser Lys Ala Asn Asn His Ala Ile Tyr Tyr Ala Glu Ser
1               5                   10                  15

Val Lys Gly

<210> SEQ ID NO 29
<211> LENGTH: 3
<212> TYPE: PRT
<213> ORGANISM: Artificial Sequence
<220> FEATURE:
<223> OTHER INFORMATION: Synthetic 297-2F3 HCDR3

<400> SEQUENCE: 29

Phe Ala Tyr
1

<210> SEQ ID NO 30
<211> LENGTH: 114
<212> TYPE: PRT
<213> ORGANISM: Artificial Sequence
<220> FEATURE:
<223> OTHER INFORMATION: Synthetic humanized 297-2F3 VL

<400> SEQUENCE: 30

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Leu Ser
                20                  25                  30

Asn Gly Asn Thr Tyr Leu Asn Trp Phe Gln Gln Arg Pro Gly Gln Ser
            35                  40                  45

Pro Arg Leu Leu Ile Tyr Lys Ile Ser Ala Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Ala His Val Pro Trp Thr Phe Gly Gly Gly Thr Lys Val Glu Ile Lys
```

Arg Thr

```
<210> SEQ ID NO 31
<211> LENGTH: 114
<212> TYPE: PRT
<213> ORGANISM: Artificial Sequence
<220> FEATURE:
<223> OTHER INFORMATION: Synthetic humanized 297-2F3 VH

<400> SEQUENCE: 31
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Lys Ala Asn Asn His Ala Ile Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Gly Phe Ala Tyr Trp Gly Gln Gly Thr Leu Val Thr Val
            100                 105                 110

Ser Ser

```
<210> SEQ ID NO 32
<211> LENGTH: 12
<212> TYPE: PRT
<213> ORGANISM: Artificial Sequence
<220> FEATURE:
<223> OTHER INFORMATION: Synthetic 211-12 epitope1

<400> SEQUENCE: 32
```

Phe Thr Leu Glu Asn Phe Ser Lys Trp Arg Gly Ser
1               5                   10

```
<210> SEQ ID NO 33
<211> LENGTH: 12
<212> TYPE: PRT
<213> ORGANISM: Artificial Sequence
<220> FEATURE:
<223> OTHER INFORMATION: Synthetic 211-12 epitope1

<400> SEQUENCE: 33
```

Glu Asn Phe Ser Lys Trp Arg Gly Ser Val Leu Ser
1               5                   10

```
<210> SEQ ID NO 34
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 34
```

Val Gln Glu His Glu Lys Tyr Ile Glu Tyr Tyr Leu
1               5                   10

```
<210> SEQ ID NO 35
<211> LENGTH: 12
```

```
<212> TYPE: PRT
<213> ORGANISM: Artificial Sequence
<220> FEATURE:
<223> OTHER INFORMATION: Synthetic partial peptide of human ADAM28s

<400> SEQUENCE: 35

His Glu Lys Tyr Ile Glu Tyr Tyr Leu Val Leu Asp
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 36

Tyr Ile Glu Tyr Tyr Leu Val Leu Asp Asn Gly Glu
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 37

Tyr Tyr Leu Val Leu Asp Asn Gly Glu Phe Lys Arg
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 38

Val Leu Asp Asn Gly Glu Phe Lys Arg Tyr Asn Glu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 39

Asn Gly Glu Phe Lys Arg Tyr Asn Glu Asn Gln Asp
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 40

Phe Lys Arg Tyr Asn Glu Asn Gln Asp Glu Ile Arg
1               5                   10

<210> SEQ ID NO 41
<211> LENGTH: 12
<212> TYPE: PRT
```

```
<213> ORGANISM: Artificial Sequence
<220> FEATURE:
<223> OTHER INFORMATION: Synthetic partial peptide of human ADAM28s

<400> SEQUENCE: 41

Tyr Asn Glu Asn Gln Asp Glu Ile Arg Lys Arg Val
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 42

Asn Gln Asp Glu Ile Arg Lys Arg Val Phe Glu Met
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 43

Glu Ile Arg Lys Arg Val Phe Glu Met Ala Asn Tyr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 44

Lys Arg Val Phe Glu Met Ala Asn Tyr Val Asn Met
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 45

Phe Glu Met Ala Asn Tyr Val Asn Met Leu Tyr Lys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 46

Ala Asn Tyr Val Asn Met Leu Tyr Lys Lys Leu Asn
1               5                   10

<210> SEQ ID NO 47
<211> LENGTH: 12
<212> TYPE: PRT
<213> ORGANISM: Artificial Sequence
```

```
<220> FEATURE:
<223> OTHER INFORMATION: Synthetic partial peptide of human ADAM28s

<400> SEQUENCE: 47

Val Asn Met Leu Tyr Lys Lys Leu Asn Thr His Val
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 48

Leu Tyr Lys Lys Leu Asn Thr His Val Ala Leu Val
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 49

Lys Leu Asn Thr His Val Ala Leu Val Gly Met Glu
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 50

Thr His Val Ala Leu Val Gly Met Glu Ile Trp Thr
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 51

Ala Leu Val Gly Met Glu Ile Trp Thr Asp Lys Asp
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 52

Gly Met Glu Ile Trp Thr Asp Lys Asp Lys Ile Lys
1               5                   10

<210> SEQ ID NO 53
<211> LENGTH: 12
<212> TYPE: PRT
<213> ORGANISM: Artificial Sequence
<220> FEATURE:
```

<223> OTHER INFORMATION: Synthetic partial peptide of human ADAM28s

<400> SEQUENCE: 53

Ile Trp Thr Asp Lys Asp Lys Ile Lys Ile Thr Pro
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 54

Asp Lys Asp Lys Ile Lys Ile Thr Pro Asn Ala Ser
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 55

Lys Ile Lys Ile Thr Pro Asn Ala Ser Phe Thr Leu
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 56

Ile Thr Pro Asn Ala Ser Phe Thr Leu Glu Asn Phe
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 57

Asn Ala Ser Phe Thr Leu Glu Asn Phe Ser Lys Trp
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 58

Phe Thr Leu Glu Asn Phe Ser Lys Trp Arg Gly Ser
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthetic partial peptide of human ADAM28s

```
<400> SEQUENCE: 59

Glu Asn Phe Ser Lys Trp Arg Gly Ser Val Leu Ser
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 60

Ser Lys Trp Arg Gly Ser Val Leu Ser Arg Arg Lys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 61

Arg Gly Ser Val Leu Ser Arg Arg Lys Arg His Asp
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 62

Val Leu Ser Arg Arg Lys Arg His Asp Ile Ala Gln
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 63

Arg Arg Lys Arg His Asp Ile Ala Gln Leu Ile Thr
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 64

Arg His Asp Ile Ala Gln Leu Ile Thr Ala Thr Glu
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthetic partial peptide of human ADAM28s
```

<400> SEQUENCE: 65

Ile Ala Gln Leu Ile Thr Ala Thr Glu Leu Ala Gly
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 66

Leu Ile Thr Ala Thr Glu Leu Ala Gly Thr Thr Val
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 67

Ala Thr Glu Leu Ala Gly Thr Thr Val Gly Leu Ala
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 68

Leu Ala Gly Thr Thr Val Gly Leu Ala Phe Met Ser
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 69

Thr Thr Val Gly Leu Ala Phe Met Ser Thr Met Cys
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 70

Gly Leu Ala Phe Met Ser Thr Met Cys Ser Pro Tyr
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 71

```
Phe Met Ser Thr Met Cys Ser Pro Tyr Ser Val Gly
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 72

Thr Met Cys Ser Pro Tyr Ser Val Gly Val Val Gln
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 73

Ser Pro Tyr Ser Val Gly Val Val Gln Asp His Ser
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 74

Ser Val Gly Val Val Gln Asp His Ser Asp Asn Leu
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 75

Val Val Gln Asp His Ser Asp Asn Leu Leu Arg Val
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 76

Asp His Ser Asp Asn Leu Leu Arg Val Ala Gly Thr
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 77
```

Asp Asn Leu Leu Arg Val Ala Gly Thr Met Ala His
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 78

Leu Arg Val Ala Gly Thr Met Ala His Glu Met Gly
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 79

Ala Gly Thr Met Ala His Glu Met Gly His Asn Phe
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 80

Met Ala His Glu Met Gly His Asn Phe Gly Met Phe
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 81

Glu Met Gly His Asn Phe Gly Met Phe His Asp Asp
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 82

His Asn Phe Gly Met Phe His Asp Asp Tyr Ser Cys
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 83

Gly Met Phe His Asp Asp Tyr Ser Cys Lys Cys Pro

<210> SEQ ID NO 84
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 84

His Asp Asp Tyr Ser Cys Lys Cys Pro Ser Thr Ile
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 85

Tyr Ser Cys Lys Cys Pro Ser Thr Ile Cys Val Met
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 86

Lys Cys Pro Ser Thr Ile Cys Val Met Asp Lys Ala
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 87

Ser Thr Ile Cys Val Met Asp Lys Ala Leu Ser Phe
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 88

Cys Val Met Asp Lys Ala Leu Ser Phe Tyr Ile Pro
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 89

Asp Lys Ala Leu Ser Phe Tyr Ile Pro Thr Asp Phe
1               5                   10

```
<210> SEQ ID NO 90
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 90

Leu Ser Phe Tyr Ile Pro Thr Asp Phe Ser Ser Cys
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 91

Tyr Ile Pro Thr Asp Phe Ser Ser Cys Ser Arg Leu
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 92

Thr Asp Phe Ser Ser Cys Ser Arg Leu Ser Tyr Asp
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 93

Ser Ser Cys Ser Arg Leu Ser Tyr Asp Lys Phe Phe
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 94

Ser Arg Leu Ser Tyr Asp Lys Phe Phe Glu Asp Lys
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 95

Ser Tyr Asp Lys Phe Phe Glu Asp Lys Leu Ser Asn
1               5                   10
```

<210> SEQ ID NO 96
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 96

Lys Phe Phe Glu Asp Lys Leu Ser Asn Cys Leu Phe
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 97

Glu Asp Lys Leu Ser Asn Cys Leu Phe Asn Ala Pro
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 98

Leu Ser Asn Cys Leu Phe Asn Ala Pro Leu Pro Thr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 99

Cys Leu Phe Asn Ala Pro Leu Pro Thr Asp Ile Ile
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 100

Asn Ala Pro Leu Pro Thr Asp Ile Ile Ser Thr Pro
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 101

Leu Pro Thr Asp Ile Ile Ser Thr Pro Ile Cys Gly
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 102

Asp Ile Ile Ser Thr Pro Ile Cys Gly Asn Gln Leu
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 103

Ser Thr Pro Ile Cys Gly Asn Gln Leu Val Glu Met
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 104

Ile Cys Gly Asn Gln Leu Val Glu Met Gly Glu Asp
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 105

Asn Gln Leu Val Glu Met Gly Glu Asp Cys Asp Cys
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 106

Val Glu Met Gly Glu Asp Cys Asp Cys Gly Thr Ser
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 107

Gly Glu Asp Cys Asp Cys Gly Thr Ser Glu Glu Cys
1               5                   10

<210> SEQ ID NO 108

```
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 108

Cys Asp Cys Gly Thr Ser Glu Glu Cys Thr Asn Ile
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 109

Gly Thr Ser Glu Glu Cys Thr Asn Ile Cys Cys Asp
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 110

Glu Glu Cys Thr Asn Ile Cys Cys Asp Ala Lys Thr
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 111

Thr Asn Ile Cys Cys Asp Ala Lys Thr Cys Lys Ile
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 112

Cys Cys Asp Ala Lys Thr Cys Lys Ile Lys Ala Thr
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 113

Ala Lys Thr Cys Lys Ile Lys Ala Thr Phe Gln Cys
1               5                   10

<210> SEQ ID NO 114
<211> LENGTH: 12
```

```
<212> TYPE: PRT
<213> ORGANISM: Artificial Sequence
<220> FEATURE:
<223> OTHER INFORMATION: Synthetic partial peptide of human ADAM28s

<400> SEQUENCE: 114

Cys Lys Ile Lys Ala Thr Phe Gln Cys Ala Leu Gly
1               5                   10

<210> SEQ ID NO 115
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 115

Lys Ala Thr Phe Gln Cys Ala Leu Gly Glu Cys Cys
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 116

Phe Gln Cys Ala Leu Gly Glu Cys Cys Glu Lys Cys
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 117

Ala Leu Gly Glu Cys Cys Glu Lys Cys Gln Phe Lys
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 118

Glu Cys Cys Glu Lys Cys Gln Phe Lys Lys Ala Gly
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 119

Glu Lys Cys Gln Phe Lys Lys Ala Gly Met Val Cys
1               5                   10

<210> SEQ ID NO 120
<211> LENGTH: 12
<212> TYPE: PRT
```

```
<213> ORGANISM: Artificial Sequence
<220> FEATURE:
<223> OTHER INFORMATION: Synthetic partial peptide of human ADAM28s

<400> SEQUENCE: 120

Gln Phe Lys Lys Ala Gly Met Val Cys Arg Pro Ala
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 121

Lys Ala Gly Met Val Cys Arg Pro Ala Lys Asp Glu
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 122

Met Val Cys Arg Pro Ala Lys Asp Glu Cys Asp Leu
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 123

Arg Pro Ala Lys Asp Glu Cys Asp Leu Pro Glu Met
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 124

Lys Asp Glu Cys Asp Leu Pro Glu Met Cys Asn Gly
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 125

Cys Asp Leu Pro Glu Met Cys Asn Gly Lys Ser Gly
1               5                   10

<210> SEQ ID NO 126
<211> LENGTH: 12
<212> TYPE: PRT
<213> ORGANISM: Artificial Sequence
```

```
<220> FEATURE:
<223> OTHER INFORMATION: Synthetic partial peptide of human ADAM28s

<400> SEQUENCE: 126

Pro Glu Met Cys Asn Gly Lys Ser Gly Asn Cys Pro
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 127

Cys Asn Gly Lys Ser Gly Asn Cys Pro Asp Asp Arg
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 128

Lys Ser Gly Asn Cys Pro Asp Asp Arg Phe Gln Val
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 129

Asn Cys Pro Asp Asp Arg Phe Gln Val Asn Gly Phe
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 130

Asp Asp Arg Phe Gln Val Asn Gly Phe Pro Cys His
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 131

Phe Gln Val Asn Gly Phe Pro Cys His His Gly Lys
1               5                   10

<210> SEQ ID NO 132
<211> LENGTH: 12
<212> TYPE: PRT
<213> ORGANISM: Artificial Sequence
<220> FEATURE:
```

<223> OTHER INFORMATION: Synthetic partial peptide of human ADAM28s

<400> SEQUENCE: 132

Asn Gly Phe Pro Cys His His Gly Lys Gly His Cys
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 133

Pro Cys His His Gly Lys Gly His Cys Leu Met Gly
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 134

His Gly Lys Gly His Cys Leu Met Gly Thr Cys Pro
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 135

Gly His Cys Leu Met Gly Thr Cys Pro Thr Leu Gln
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 136

Leu Met Gly Thr Cys Pro Thr Leu Gln Glu Gln Cys
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 137

Thr Cys Pro Thr Leu Gln Glu Gln Cys Thr Glu Leu
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 138

Thr Leu Gln Glu Gln Cys Thr Glu Leu Trp Gly Pro
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 139

Glu Gln Cys Thr Glu Leu Trp Gly Pro Gly Arg Arg
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 140

Thr Glu Leu Trp Gly Pro Gly Arg Arg Thr Asn Pro
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 141

Trp Gly Pro Gly Arg Arg Thr Asn Pro Phe Pro Cys
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 142

Gly Arg Arg Thr Asn Pro Phe Pro Cys Ala Cys Ala
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Synthetic partial peptide of human ADAM28s

<400> SEQUENCE: 143

Thr Asn Pro Phe Pro Cys Ala Cys Ala Lys Glu Asn
1               5                   10

<210> SEQ ID NO 144
<211> LENGTH: 12
<212> TYPE: PRT
<213> ORGANISM: Artificial Sequence
<220> FEATURE:
<223> OTHER INFORMATION: Synthetic partial peptide of human ADAM28s

```
<400> SEQUENCE: 144

Phe Pro Cys Ala Cys Ala Lys Glu Asn His Phe Arg
1               5                   10

<210> SEQ ID NO 145
<211> LENGTH: 9
<212> TYPE: PRT
<213> ORGANISM: Artificial Sequence
<220> FEATURE:
<223> OTHER INFORMATION: Synthetic partial peptide of human ADAM28s

<400> SEQUENCE: 145

Cys Leu Phe Asn Ala Pro Leu Pro Thr
1               5

<210> SEQ ID NO 146
<211> LENGTH: 114
<212> TYPE: PRT
<213> ORGANISM: Artificial Sequence
<220> FEATURE:
<223> OTHER INFORMATION: Synthetic 297-2F3 VH

<400> SEQUENCE: 146

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Ile Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Phe Ala Tyr Trp Gly Gln Gly Thr Leu Val Thr Val
            100                 105                 110

Ser Ala

<210> SEQ ID NO 147
<211> LENGTH: 114
<212> TYPE: PRT
<213> ORGANISM: Artificial Sequence
<220> FEATURE:
<223> OTHER INFORMATION: Synthetic 297-2F3 VL

<400> SEQUENCE: 147

Asp Val Val Met Thr Gln Thr Pro Leu Ser Leu Pro Val Ser Leu Gly
1               5                   10                  15

Asp Lys Ala Ser Ile Ser Cys Arg Ser Ser Gln Ser Leu Val Leu Ser
            20                  25                  30

Asn Gly Asn Thr Tyr Leu Asn Trp Tyr Leu Gln Lys Pro Gly Gln Ser
        35                  40                  45

Pro Lys Leu Leu Ile Tyr Lys Ile Ser Ala Arg Phe Ser Gly Val Pro
    50                  55                  60
```

-continued

```
Asp Arg Phe Ser Gly Ser Gly Ser Gly Thr Asp Phe Thr Leu Arg Ile
 65          70              75                  80

Ser Arg Val Glu Ala Glu Asp Leu Gly Val Tyr Phe Cys Ser Gln Thr
             85              90                  95

Ala His Val Pro Trp Thr Phe Gly Gly Gly Thr Lys Leu Glu Ile Lys
             100             105             110

Arg Ala
```